(12) United States Patent
Cornwall et al.

(10) Patent No.: US 7,700,640 B2
(45) Date of Patent: Apr. 20, 2010

(54) PROCESS FOR MAKING PHENOXY BENZAMIDE COMPOUNDS

(75) Inventors: Philip Cornwall, Leicestershire (GB); David Simon Ennis, Leicestershire (GB); Melvyn Edward Giles, Leicestershire (GB); Jacob Robert James Perkins, Leicestershire (GB); Shelly Louise Jenkin, Bristol (GB); Jeremy Stephen Parker, Bristol (GB); Bharti Patel, Bristol (GB)

(73) Assignee: AstraZeneca AB, Sodertalje (SE)

( * ) Notice: Subject to any disclaimer, the term of this patent is extended or adjusted under 35 U.S.C. 154(b) by 165 days.

(21) Appl. No.: 11/665,247

(22) PCT Filed: Oct. 11, 2005

(86) PCT No.: PCT/GB2005/003882

§ 371 (c)(1),
(2), (4) Date: Oct. 9, 2007

(87) PCT Pub. No.: WO2006/040527

PCT Pub. Date: Apr. 20, 2006

(65) Prior Publication Data

US 2008/0200694 A1    Aug. 21, 2008

(30) Foreign Application Priority Data

Oct. 16, 2004 (GB) ............................ 0423042.1
Feb. 12, 2005 (GB) ............................ 0502963.2

(51) Int. Cl.
*A61K 31/415* (2006.01)
*C07D 231/38* (2006.01)
(52) U.S. Cl. .................... 514/407; 548/372.5
(58) Field of Classification Search ............ 548/372.5
See application file for complete search history.

(56) References Cited

U.S. PATENT DOCUMENTS

| | | | |
|---|---|---|---|
| 2,750,393 A | 6/1956 | Elpern | |
| 2,967,194 A | 1/1961 | Murray | |
| 3,917,625 A | 11/1975 | Lee et al. | |
| 3,950,351 A | 4/1976 | Rossignol et al. | |
| 4,009,174 A | 2/1977 | Cluzan et al. | |
| 4,105,785 A | 8/1978 | Mauvernay et al. | |
| 4,146,631 A | 3/1979 | Ford et al. | |
| 4,434,170 A | 2/1984 | Dostert et al. | |
| 4,474,792 A | 10/1984 | Erickson | |
| 4,634,783 A | 1/1987 | Fujii et al. | |
| 4,966,891 A | 10/1990 | Fujiu et al. | |
| 5,258,407 A | 11/1993 | Washburn et al. | |
| 5,273,986 A | 12/1993 | Holland et al. | |
| 5,399,702 A | 3/1995 | Holland et al. | |
| 5,466,715 A | 11/1995 | Washburn et al. | |
| 5,510,478 A | 4/1996 | Sabb | |
| 5,661,153 A | 8/1997 | Isobe et al. | |
| 5,672,750 A | 9/1997 | Perry | |

(Continued)

FOREIGN PATENT DOCUMENTS

CA    2605738    11/2006

(Continued)

OTHER PUBLICATIONS

Brenner et al. "Imino-bridged heterocycles. VII. (1) N-aminobenzocycloheptapyridinimines" J. Heterocyclic Chem. 23:1331-1332 (1986).

(Continued)

*Primary Examiner*—Kamal A Saeed
*Assistant Examiner*—Kristin Bianchi
(74) *Attorney, Agent, or Firm*—Morgan, Lewis & Bockius LLP

(57) ABSTRACT

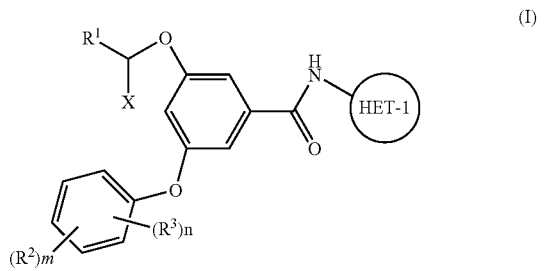

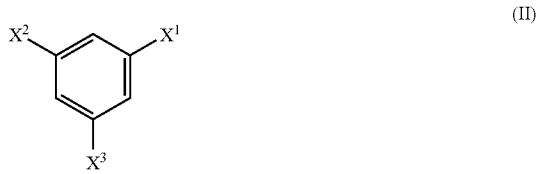

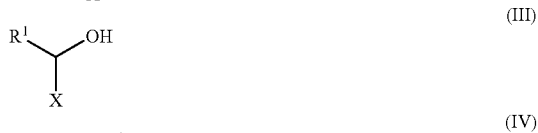

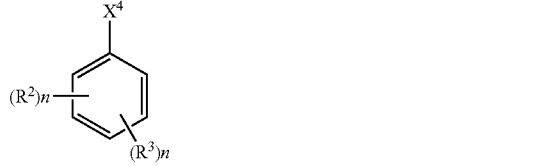

A process for making a compound of formula (I), said process comprising a) reacting a compound of formula (II) with: i) a compound of formula (III) by nucleophilic aromatic substitution of $X^2$ and ii) a compound of formula (IV) for example by nucleophilic aromatic substitution b) where necessary, converting $X^1$ to a carboxylic acid; and c) coupling of the carboxylic acid group to an appropriate heterocyclic amine; wherein all variables are as defined in the description.

15 Claims, No Drawings

U.S. PATENT DOCUMENTS

| | | | |
|---|---|---|---|
| 5,712,270 A | 1/1998 | Sabb | |
| 5,849,735 A | 12/1998 | Albright et al. | |
| 6,110,945 A | 8/2000 | Head et al. | |
| 6,197,798 B1 | 3/2001 | Fink et al. | |
| 6,200,995 B1 | 3/2001 | De la Brouse-Elwood et al. | |
| 6,207,693 B1 | 3/2001 | Setoi et al. | |
| 6,214,878 B1 | 4/2001 | Bernardon et al. | |
| 6,242,474 B1 | 6/2001 | Yamasaki et al. | |
| 6,255,335 B1 | 7/2001 | Himmler et al. | |
| 6,316,482 B1 | 11/2001 | Setoi et al. | |
| 6,320,050 B1 | 11/2001 | Bizzarro et al. | |
| 6,348,474 B1 | 2/2002 | Kayakiri et al. | |
| 6,369,229 B1 | 4/2002 | Head et al. | |
| 6,376,515 B2 | 4/2002 | Zhu et al. | |
| 6,388,071 B2 | 5/2002 | Mahaney | |
| 6,448,399 B1 | 9/2002 | Corbett et al. | |
| 6,486,349 B1 | 11/2002 | Flitter et al. | |
| 6,528,543 B1 | 3/2003 | Bizzarro et al. | |
| 6,545,155 B2 | 4/2003 | Corbett et al. | |
| 6,610,846 B1 | 8/2003 | Bizzarro et al. | |
| 6,613,942 B1 | 9/2003 | Ling et al. | |
| 7,132,546 B2 | 11/2006 | Kato et al. | |
| 7,199,140 B2 | 4/2007 | Hayter et al. | |
| 7,230,108 B2 | 6/2007 | Hargreaves et al. | |
| 7,432,287 B2 * | 10/2008 | Iino et al. | 514/340 |
| 2001/0027200 A1 | 10/2001 | De la Brouse-Elwood et al. | |
| 2002/0002183 A1 | 1/2002 | Zhu et al. | |
| 2002/0095044 A1 | 7/2002 | Jagtap et al. | |
| 2003/0162690 A1 | 8/2003 | Zhu et al. | |
| 2004/0014968 A1 | 1/2004 | Bizzarro et al. | |
| 2004/0077555 A1 | 4/2004 | Ishihara et al. | |
| 2005/0080106 A1 | 4/2005 | Boyd et al. | |
| 2005/0148605 A1 | 7/2005 | Grotzfeld et al. | |
| 2005/0165074 A1 | 7/2005 | Grotzfeld et al. | |
| 2005/0171171 A1 | 8/2005 | Mehta et al. | |
| 2005/0171172 A1 | 8/2005 | Lai et al. | |
| 2005/0261315 A1 | 11/2005 | Mehta et al. | |
| 2006/0004010 A1 | 1/2006 | Habashita et al. | |
| 2006/0167053 A1 | 7/2006 | Iino et al. | |
| 2006/0258728 A1 | 11/2006 | Tani et al. | |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1400540 | 11/2000 |
| EP | 1132381 | 9/2001 |
| EP | 0620216 | 1/2003 |
| EP | 1336607 | 8/2003 |
| EP | 1357116 | 10/2003 |
| EP | 1496052 | 1/2005 |
| EP | 1 600 442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/36480 | 3/1997 |
| WO | WO 97/24355 | 7/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |

| | | |
|---|---|---|
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 94/04525 | 3/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Coghlan et al. "Glucokinase activators in diabetes management" Expert Opin. Investig. Drugs 17(2):145-167 (2008).
Leighton, "Pre-clinical disease models—challenges and success stories" 44th Drug Information Association Annual Meeting, Boston, MA, US (2008).
Lith, "Evaluation of the effects on whole body glucose metabolism after single doses of X2000—A glucose lowering agent" Poster presentation, Master thesis in Pharmaceutical Bioscience, Goteborgs University (2008).
Ralph et al. "Glucose Modulation of Glucokinase Activation by Small Molecules" Biochemistry 47(17):5028-5036 (2008).
Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).
Sarabu et al., "Glucokinase activators as new type 2 diabetes therapeutic agents" Expert Opinion on Therapeutic Patents 18(7):759-768 (2008).
Shorvon, "Pyrrolidone derivatives" Lancet 358(9296):1885-1892 (2001).
Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin, Trans. 2, p. 929.
West, Anthony R., "Solid State Chemistry and its Applications" Wiley, New York, pp. 358 and 365 (1988).
Wolff, Manfred E. "Burger's Medicinal Chemistry", 5th Edition, Part I, John Wiley & Sons, pp. 975-977 (1995).
Alvarez et al. "Evidence that glucokinase regulatory protein is expressed and interacts with glucokinase in rat brain" J. Neurochem. 80(1):45-53 (2002).
Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the Pyrido[2,3-d]pyrimidine series" J. Org. Chem. 42(6):993-996 (1977).
Ando et al. "Fluoride salts on alumina as reagents for alkylation of phenols and alcohols" Bull. Chem. Soc. Jpn., 55:2504-2507 (1982).
Atwell, G. J. et al. "Potential antitumor agents. VI. Bisquaternary salts" J. Med. Chem. 11(2):295-300 (1968).
Baker, R. et al. "Structure and synthesis of Pallescansin E utilizing a modified Wadsworth-Emmons reaction" J. Chem. Soc., Perkin Trans. 1, 12, pp. 3087-3091 (1981).
Baker, R. et al. "Synthesis of Pallescensin-E: use of crown ether in the Wadsworth procedure for olefin formation" Tetrahedron Lett. 22, pp. 161-162 (1981).
Balant et al. "Metabolic considerations, etc." Burger's Medicinal Chemistry, 5th edition, 1, Wollf ed. NY: John Wiley & Sons, p. 949-982 (1995).
Beilstein Registry No. 6511458 (Apr. 18, 1994), [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42:3514-3518 (1977).
Berl et al. "Induced fit selection of a barbiturate receptor from a dynamic configurational/conformational library" European J. Org. Chem. (11):3089-3094 (1999).
Berl et al. "Template-induced and molecular recognition directed hierarchical generation of supramolecular assemblies from molecular strands" Chem. Eur. J., 6(11): 1938-1946 (2000).
Bonina, F. et al. "Synthesis and pharmacologic activity of 2-arylethenylthiazol-4-acetic and 4-carboxylic acids" Farmaco, 40(11), p. 875-884 (1985).

Boucherle et al. "Recherches dans la serie des cetones polyphenoliques IV. Thiazoles" Chimica. Therapeutica., 3(5):360-363 (1968) (Translation enclosed).

Bowden et al. "Structure-activity relations. Part 10. Metal-ion-complexation studies of a series of substituted benzamidotetrazoles" J. Chem. Research (Synopses) 11:304 (1991).

Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).

Brocklehurst et al. "Stimulation of Hepatocyte Glucose Metabolism by Novel Small Molecule Glucokinase Activators" Diabetes 53:535-541 (2004).

Caro et al. "Liver glucokinase: decreased activity in patients with type II diabetes" Horm. Metab. Res., 27(1):19-22 (1995).

Carroll et al. "The in vitro characterisation of a novel Glucokinase activator" Stress, Signalling and Control, Biochemical Society Meeting 679, University of Essex, UK (Jul. 2-4, 2003).

Caulfield et al. "The first potent and selective inhibitors of the glycine transporter type 2" J. Med. Chem., 44(17): 2679-2682 (2001).

Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica, 13(6): 539-543 (1978) (Translation enclosed).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Christesen et al. "The second activating glucokinase mutation (A456V): Implications for glucose homeostasis and diabetes therapy" Diabetes, 51(4):1240-1246 (2002).

Ciaceri, G. et al. "Analgesic, antipyretic and antiphlogistic effect of several new acids of the phenylethylene-thiazole series" Minerva Med., 63(42), p. 2409-2413 (1972).

Coburn et al. "Mesoionic purinone analogs. IV. Synthesis and in vitro antibacterial properties of mesoionic thiazolo(3,2-a)pyrimidin-5,7-diones and mesoionic 1,3,4-thiadizolo(3,2-a)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coope et al. "Predictive blood glucose lowering efficacy by Glucokinase activators in high fat fed female Zucker rats", Br. J. Pharmacol., 149(3):328-335 (2006).

Corbett, "Track 3-mastering medicinal chemistry: applying organic chemistry to biological problems, success stories in medicinal chemistry" Molecular Medicine Tri-Conference, Moscone West Convention Center, San Francisco California, 11:00-11:30, Glucokinase Activator: Discovery of Novel, Orally Active Glucse Lowering Agents, Mar. 24-26, 2004.

Corbett, "Glucokinase activators: discovery of novel, orally active glucose lowering agents" Cambridge healthtech Institute's Eleventh Annual Molecular Medicine Tri-Conference, San Francisco, CA, Mar. 24-26, 2004.

Cushman et al. "Synthesis and evaluation of new protein-tyrosine kinase inhibitors. Part 1. pyridine-containing stilbenes and amides" Bioorganic & Medicinal Chemistry Letters, 1(4):211-214 (1991).

DeFronzo et al. "The triumvirate: β-cell, muscle, liver. A collusion responsible for NIDDM" Diabetes 37:667-687 (1988).

DeJohn, et al., "Functionalization of Substituted 2(1H)- and 4(1H)-Pyridones. III. The Preparation of Substituted 6-Vinyl-1,2-dihydro-2-oxo—and 1,4-Dihydro-4-oxo-3-pyridinecarboxylic Acids through the Chemistry of Pyridone Dianions", J. Heterocyclic Chem., 20(5), p. 1295-1302 (1983).

De Paulis, T. et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem., 25: 507-517 (1990).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem., 22: 1686 (1957).

Ferre et al. "Correction of diabetic alterations by glucokinase" PNAS USA. 93(14): 7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem., 29(4):538-549 (1986).

Froguel et al. "Familial hyperglycemia due to mutations in glucokinase—Definition of a subtype of diabetes mellitus" New Engl. J. Med., 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group Abstract (Nov. 2005).

Gill et al. "Upregulation of Key β-cell Genes and Improvement of Function in Rodent Islets Following Chronic In Vitro Treatment with a Glucokinase Activator" Diabetologia, vol. 50, S218 (2007).

Gill et al. "Stimulation of Insulin Release in MIN6 Cells and Isolated Rodent Islets by a Small Molecule Glucokinase Activator (GKA50)" Diabetologia, vol. 49 (Suppl 1), 0501 (2006).

Glaser et al. "Familial hyperinsulinism caused by an activating glucokinase mutation" The New England Journal of Medicine, 338(4):226-230 (1998).

Gorman, et al. "Effect of High-Fat Diet on Glucose Homeostasis and Gene Expression in Glucokinase (GK) Heterozygous Knock-Outs" abstract of the oral presentation, American Diabetes Association, Jun. 2007.

Grimsby "Glucokinase activators-potential treatment for type 2 diabetes" Roche, SMi Diabetes, London, UK, p. 28-29 (2002).

Grimsby et al. "Allosteric activators of glucokinase: potential role in diabetes therapy" Science 301(5631):370-373 (2003).

Grimsby, J. "Potential treatment for type 2 diabetes" Roche in-house Literature.

Guertin et al. "Small Molecule Glucokinase Activators as Glucose Lowering Agents: A New Paradigm for Diabetes Therapy" Current Medicinal Chemistry, 13(15): 1839-1843 (2006).

Hashimoto, Y. et al. "Evaluation of differentiation-inducing activity of retinoids on human leukemia cell lines Hl-60 and NB4", Biol. Pharm. Bull., 19(10): 1322-1328 (1996).

Hirst, S. et al. "Molecular recognition of phosphate esters: a balance of hydrogen bonding and proton transfer interactions" Israel Journal of Chemistry, 32: 105-111 (1992).

Horsak, I. et al. "Method of evaluation of the phase diagram of a system with formation of a compound" Chem. Zvesti., 36(3), (1982).

Isomura, K. et al. "Z-type deposition of a polymerizable amphiphile to fabricate an immobilized LB film showing strong second harmonic generation" Thin Solid Films, 244, (1994).

Japanese unexamined patent JP 8301760 "Rising sun communications".

Johnson et al. "Glucose-Dependent Modulation of Insulin Secretion and Intracellular Calcium Ions by GKA50—A Glucokinase Activator" abstract of the oral presentation, American Diabetes Association, Jun. 2007.

Julia et al. Synthesis of a 2,3,4,4a,5,6-hexahydrobenzo[f]quinoline system by "aryne substitution" Bull Chem Soc France, vol. 11, 4463-4467 (1968) (Translation enclosed).

Kamata, T. et al. "Pyroelectricity of noncentrosymmetric Langmuir-Blodgett films of phenylpyrazine derivatives" Jpn. J. Appl. Phys., 33(2), p. 1074-1078 (1994).

Kar A. "Cinchophen analogues as potential CNS agents" J Pharm Sci., 72(9):1082-1084 (1983).

Kennedy, "Interchim intermediated" Database Chemcats Online: Chemical Abstracts Service XP002272449 (2002).

Knoppova, V. et al. "Synthesis and properties of 5-styryl-2-furancarboxlic acids" Collection Czechoslovak Chem. Commun., vol. 46, (1981).

Konig et al. "Binding of Heptanedioic Acid to a Threefold Pyridine Arylamide Receptor. Enhancement of the Stability of Supramolecular Solution Structures by Multiple Binding Sites" J. Org. Chem., 60(13):4291-4293 (1995).

Kunishima et al. "4-(4,6-Dimethoxy-1,3,5-triazin-2-y1)-4-methylmorpholinium chloride: an efficient condensing agent leading to the formation of amides and esters" Tetrahedron, 55:13159-13170 (1999).

Kurata et al. "D-Glucose suppression of eating after intra-third ventricle infusion in rat" Physiology & Behavior, 37:615-620 (1986).

Kurata et al. "Structural evaluation of glucose analogues on feeding elicitation in rat" Metabolism, 38(1):46-51 (1989).

Lai et al. "Formation of columnar arrangements in copper(ii) complexes of 2-phenylazomethinopyridine derivatives" J. Materials Chemistry, 8(11):2379-2383 (1998).

Leighton et al. "Small molecule glucokinase activators as novel antidiabetic agents" Biochem Soc Trans., 33(Pt 2):371-374 (Apr. 2005).

Leighton et al. "Improved Glycemic Control After Sub-acute Administration of a Glucokinase Activator to Male Zucker (fa/fa) Rats" abstract of the oral presentation, American Diabetes Association, Jun. 2007.

Levin et al. "Brain glucose sensing and body energy homeostasis: role in obesity and diabetes" Am. J. Physiol., 276(5 Pt 2):R1223-R1231 (1999).

Levin et al. "Differential effects of diet and obesity on high and low affinity sulfonylurea binding sites in the rat brain" Brain Research, 739(1-2):293-300 (1996).

Levin et al. "In vivo and in vitro regulation of [3H]glyburide binding to brain sulfonylurea receptors in obesity-prone and resistant rats by glucose" Brain Research, 776(1-2):146-153 (1997).

Levin et al. "Reduced glucose-induced neuronal activation in the hypothalamus of diet-induced obese rats" Brain Research, 808(2):317-319 (1998).

Levin, B. E. "Glucosensing neurons do more than just sense glucose" International Journal of Obesity, 25, suppl 5: S68-S72 (2001).

Levkoev et al. "Research on cyanide dyes 11. 7,7'-Dimethylthiacarbocyanines" Zhurnal Obshchei Khimii, 27:3097-3107 (1957) (Translation enclosed).

Lynch et al. "Localization of glucokinase gene expression in the rat brain" Diabetes, 49(5):693-700 (2000).

Mastafanova et al. "Features of the catalytic reduction of 4-(3-oxoquinuclidyl-2-methylene)-6-methoxyquinoline and its ethyleneketal" Kim Geterotsiki Soedin., (1):86-94 (1989) (Translation enclosed).

Mastafanova et al., "Synthesis, Anti-Inflammatory and Analgesic Activity of 1,6-Disubstituted Pipecolic and 6-Substituted Picolinic Acids," Khim Farm ZH, 22(4) 428-431 (1998).

Mastafanova, et al. "Synthesis and study of the antihypertensive activity of substituted N-acetylmercaptopropiony1-6-[2'-phenylethyl]pipecolinic acids" Khim Farm ZH., 22(2), p. 294-302 (1998).

Mazik et al. "Molecular recognition of carbohydrates by artificial receptors: systematic studies towards recognition motifs for carbohydrates" Chemistry, 7(3):664-670 (2001).

Mazik et al. "Molecular recognition of carbohydrates by artificial polypyridine and polypyrimidine receptors" Angewandte Chemie (International ed. in English), 39(3):551-554 (2000).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher "Design and synthesis of novel glucokinase activators" 13th RSC-SCI Medicinal Chemistry Symposium, Churchill College Cambridge (Sep. 2005).

McKerrecher et al. "Discovery, synthesis and biological evaluation of novel glucokinase activators" Bioorg Med Chem Lett., 15(8):2103-2106 (2005).

McKerrecher et al. "Identification of orally bioavailable small molecule activators of glucokinase" Abstract, Anglo-Swedish Medicinal Chemistry Meeting (Mar. 2005).

McKerrecher et al. "Design and synthesis of novel glucokinase activators as potential treatment for type 2 diabetes" Frontiers in Medicinal Chemistry, Frankfurt (Mar. 2006).

McKerrecher et al. "Design of a potent, soluble glucokinase activator with excellent in vivo efficacy" Bioorg. Med. Chem. Lett., 16(10):2705-2709 (May 15, 2006) Epub Feb. 28, 2006.

McKerrecher et al. "Design & Synthesis of Novel Glucokinase Activators as Potential Treatments for Type 2 Diabetes" 233rd ACS National Meeting, Chicago, IL, Mar. 25-29, 2007.

Meijer et al "Chiral amplification in supramolecular stacks" Polymer Preprints (Am Chem Soc, divn Polymer chemistry) 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab., 281(4):E649-E654 (2001).

Moore et al. "Acute fructose administration improves oral glucose tolerance in adults with type 2 diabetes" Diabetes Care, 24(11):1882-1887 (2001).

Motesharei et al. "Molecular Recognition in Membrane Mimics: a Fluorescence Probe" J. Am. Chem. Soc., 116(16):7413-7414 (1994).

Motesharei et al. "Molecular Recognition on Functionalized Self-Assembled Monolayers of Alkanethiols on Gold" J. Am. Chem. Soc., 120(29): 7328-7336 (1998).

Palmans "Extended-core discotic liquid crystals based on the intramolecular H-bonding in N-acylated 2,2'-bipyridine3,3'-diamine moieties" Chemistry, 3(2):300-307 (1997).

Plieninger et al. "Synthesis of 7,8-dihydro-5,6-benzoquinoline-(3)-carboxylic acid" Chem. Ber., 87:882-887 (1954) (Translation enclosed).

Printz et al. "Mammalian glucokinase" Annu. Rev. Nutr., 13:463-496 (1993).

Prousek, J. et al. "Preparation and electron transfer-induced cis-trans isomerization reactions of 1-(5-nitro-2-furyl)-, 1-(5-nitro-1-thienyl)-, and 1-(4-nitrophenyl)-2-R ethylenes" Collect. Czech. Chem. Commun., vol. 54 (1989).

Qian-Cutrone et al. "Glucolipsin A and B, two new glucokinase activators produced by *Streptomyces purpurogeniscleroticus* and *Nocardia vaccinii*" J. Antibiot (Tokyo), 52(3):245-255 (1999).

Rivalle, C. et al. "Furannes et pyrroles disubstitues en 2,3—XVIII : Synthese et rearrangement de 4H-dihydro-9,10 benzo[4,5]cyclohepta[1,2-b]furannones-4" Tetrahedron, 32(7), p. 829-834 (1976).

Rogers et al. "Mesoionic purinone analogues as inhibitors of cyclic-AMP phosphodiesterase: a comparison of several ring systems" J. Med. Chem., 24(11):1284-1287 (1981).

Roncero et al. "Functional glucokinase isoforms are expressed in rat brain" J. Neurochem., 74(5):1848-1857 (2000).

Rowe et al. "Potassium channel dysfunction in hypothalamic glucose-receptive neurones of obese Zucker rats" Journal of Physiology, 497.2:365-377 (1996).

Schuit et al. "Glucose sensing in pancreatic β-Cells. A model for the study of other glucose-regulated cells in gut, pancreas, and hypothalamus" Diabetes, 50:1-11 (2001).

Sekefa et al. "No. 69.—Recherches sur les anesthesiques locaux (XI memoire) Synthese de quelques nouveaux β-alcoxyethoxycarbanilates et β-alcoxyethoxycinchonamides amines" Bull. Chem. Soc. France., 401-404 (1959) (Translation enclosed).

Seoane et al. "Glucokinase overexpression restores glucose utilization and storage in cultured hepatocytes from male Zucker diabetic fatty rats" J Biol Chem., 274(45):31833-31838 (1999).

Shepard, K. et al. "Imino-bridged heterocycles. VII. (1) N-aminobenzocycloheptapyridinimines" J. Heterocyclic Chem., vol. 23 (1986).

Shiota et al. "Glucokinase gene locus transgenic mice are resistant to the development of obesity-induced type 2 diabetes" Diabetes, 50(3):622-629 (2001).

Spanswick et al. "Insulin activates ATP-sensitive K+ channels in hypothalamic neurons of lean, but not obese rats" Nature Neuroscience, 3(8):757-758 (2000).

Spanswick et al. "Leptin inhibits hypothalamic neurons by activation of ATP-sensitive potassium channels" Nature, 390(6659):521-525 (1997).

Stout et al. "Synthesis and antiarrhythmic and parasympatholytic properties of substituted phenols. 3. Modifications to the linkage region (region 3)" J. Med. Chem., 28(3):295-298 (1985).

Suhua et al. "Synthesis and biological activity of tyrosine protein kinase inhibitors" Acta Pharmaceutica Sinica, 32(7): 515-523 (1997).

Tecilla, P. et al. "Hydrogen-bonding self-assembly of multichromophore structures" J. Am. Chem. Soc., 112: 9408-9411 (1990).

Tecilla, P. et al. "Transition-state stabilization and molecular recognition: acceleration of phosphoryl-transfer reactions by an artificial receptor" J. Am. Chem. Soc., 112: 9586-9590 (1990).

Tecilla et al. "Synthetic hydrogen bonding receptors as models of transacylase enzymes" Tetrahedron, 51(2):435-448 (1995).

Tornetta et al. "Arylvinylthiazole derivatives with anti-inflammatory, analgesic and anti-pyretic activity" Boll Sedute Accad Giovenia Sci. Nat. Catanica, 11(9-10):89-95 (1973) (Translation enclosed).

Tucker, H. et al. "Novel Inhibitors of prolyl 4-hydroxylase. 2. 5-amide substituted pyridine-2-carboxylic acids" J. Med. Chem., 35, p. 804-807 (1992).

Van Gorp et al. "C3-symmetrical supramolecular architectures: fibers and organic gels from discotic trisamides and trisureas" J Am. Chem. Soc., 124(49):14759-14769 (2002).

Vanderstelt, C. et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch., 22(1) (1972).

Velho et al. "Impaired hepatic glycogen synthesis in glucokinase-deficient (MODY-2) subjects" J. Clin. Invest..,98(8):1755-1761 (1996).

Vertigan et al. "Impact of cell glycogen content on modulation of hepatocyte glucose metabolism by pharmacological agents" Diabetologia, 47 Supp 1, A214, 589 (2004).

Williams et al. "Meeting the Needs of Type 2 Diabetes Patients" Highlights from the society for medicines research symposium type 2 diabetes: mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance", abstract of the oral presentation, American Diabetes Association, Jun. 2007.

Winzell et al. "Glucokinase Activation Reduces Glycemia and Improves Glucose Tolerance in Mice with High-fat Diet-induced Insulin Resistance", Diabetes, vol. 56 (Supplement 1) 1482-P (2007).

Yakushijin, K. et al. "Intramolecular ring formation of phenyl azide and furan" Heterocycles, 12(8), pp. 1021-1026 (1979).

Yakushijin, K. et al. "Intramolecular ring formation of phenyl azide and furan moieties" Chem. Pharm. Bull., 30(1), (1982).

Yang et al. "Hypothalamic glucose sensor: similarities to and differences from pancreatic beta-cell mechanisms" Diabetes, 48(9):1763-1772 (1999).

Yoshina, S. et al. "Studies of heterocyclic compounds. II. Synthesis of 2-furylvinyl-benzenes and studies of polarography" Yakugaku Zasshi, 88(4), p. 398-404 (1968).

Yoshina, S. et al. "Studies of heterocyclic compounds. III. Synthesis of methyl 5-(2-phenylvinyl)2-furoate" Yakugaku Zasshi, 88(4), p. 405-409 (1968).

Yoshina, S. et al. "Studies of heterocyclic compounds. IV. Ultraviolet spectra of 2-(2-furyl)vinylbenzenes and 2-(2-furyl)vinylfurans" Yakugaku Zasshi, 88(4), p. 410-416 (1968).

Yoshina, S. et al. "Studies of heterocyclic compounds. VI. 2-(Carbomethoxy-2-furyl)vinyl benzenes and their ultraviolet spectra" Yakugaku Zasshi, 88(4), p. 977-983 (1968).

Youssefyeh et al. "Development of high-affinity 5-HT3 receptor antagonists. 1. Initial structure-activity relationship of novel benzamides" J. Med. Chem., 35(5): 895-903 (1992).

Zhang et al. "Synthesis based on affinity separation (SAS): separation of products having barbituric acid tag from untagged compounds by using hydrogen bond interaction" Synlett, 5:590-596 (2001).

* cited by examiner

PROCESS FOR MAKING PHENOXY BENZAMIDE COMPOUNDS

The present application is a U.S. National Phase Application of International Application No. PCT/GB2005/003882 (filed Oct. 11, 2005) which claims the benefit of Great Britain Patent Application No. 0423042.1 (filed Oct. 16, 2004) and Great Britain Patent Application No. 0502963.2 (filed Feb. 12, 2005), all of which are hereby incorporated by reference in their entirety.

This invention relates to an improved chemical process for making compounds which are useful in the treatment or prevention of a disease or medical condition mediated through glucokinase (GLK or GK), leading to a decreased glucose threshold for insulin secretion. Such compounds are predicted to lower blood glucose by increasing hepatic glucose uptake. Such compounds may have utility in the treatment of Type 2 diabetes and obesity. The invention is also related to intermediates useful in the improved chemical process.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-100 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In our co-pending applications (WO2005/080359, WO2005/080360, PCT/GB2005/002166 and priority applications GB0423044.7 and GB0423043.9) we have described compounds which are useful as GLK activators, which are of general chemical formula (I).

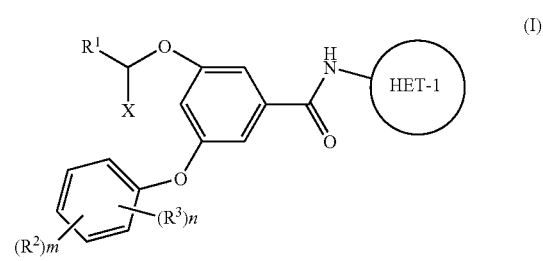

(I)

wherein for example $R^1$ is hydroxymethyl, methoxymethyl or methyl;

X is methyl or ethyl;

$R^2$ is selected from —C(O)NR$^4$R$^5$, —SO$_2$NR$^4$R$^5$, —S(O)$_p$R$^4$ and HET-2;

HET-1 is an optionally substituted 5- or 6-membered, C-linked heteroaryl ring containing a nitrogen atom in the 2-position;

HET-2 is an optionally substituted 4-, 5- or 6-membered, C- or N-linked heterocyclyl ring containing 1, 2, 3 or 4 heteroatoms;

$R^3$ is selected from halo, fluoromethyl, difluoromethyl, trifluoromethyl, methyl, methoxy and cyano;

$R^4$ is selected from hydrogen, (1-4C)alkyl [optionally substituted], (3-6C)cycloalkyl (optionally substituted) and HET-2;

$R^5$ is hydrogen or (1-4C)alkyl;

or $R^4$ and $R^5$ together with the nitrogen atom to which they are attached may form a heterocyclyl ring system;

m is 0 or 1;

n is 0, 1 or 2;

provided that when m is 0, then n is 1 or 2;

or a salt, pro-drug or solvate thereof.

The compounds of formula (I) are N-heterocyclyl-aryl amides, wherein the aryl ring is 3,5-disubstituted by a substituted alkyl ether and an aryloxy substituent. These compounds have generally been synthesised using reaction sequences such as those illustrated in Schemes 1 and 2 below:

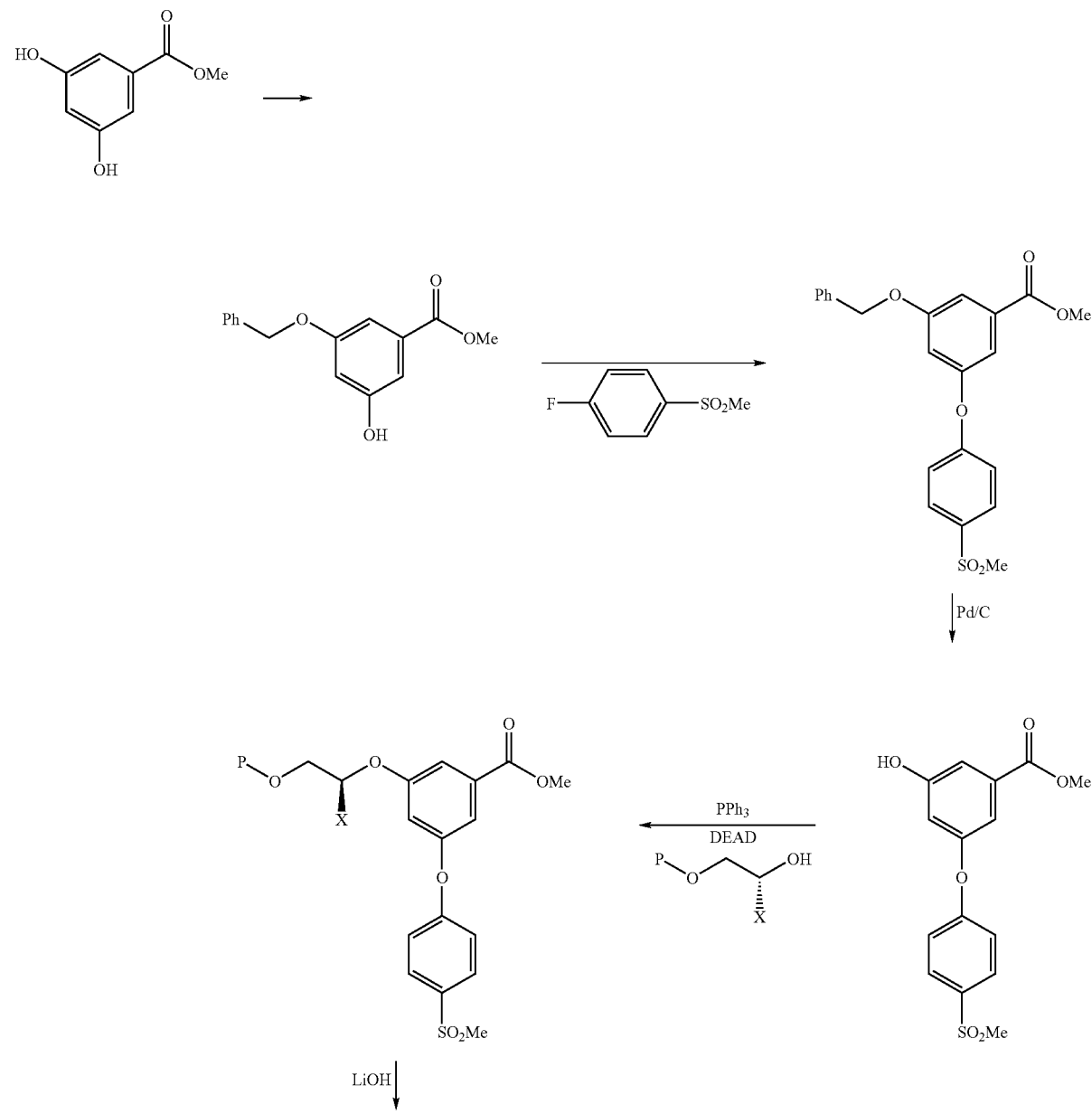

Scheme 1

-continued
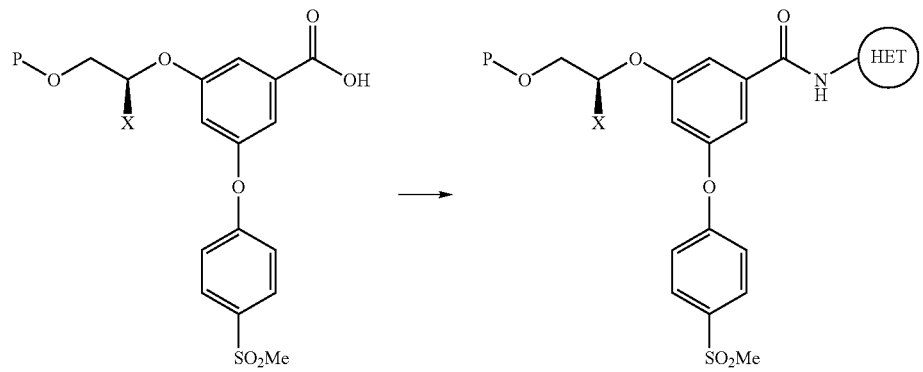
where X is as defined in Formula (1), P is methyl or a protecting group such as a trialkylsilyl group.
Scheme 2
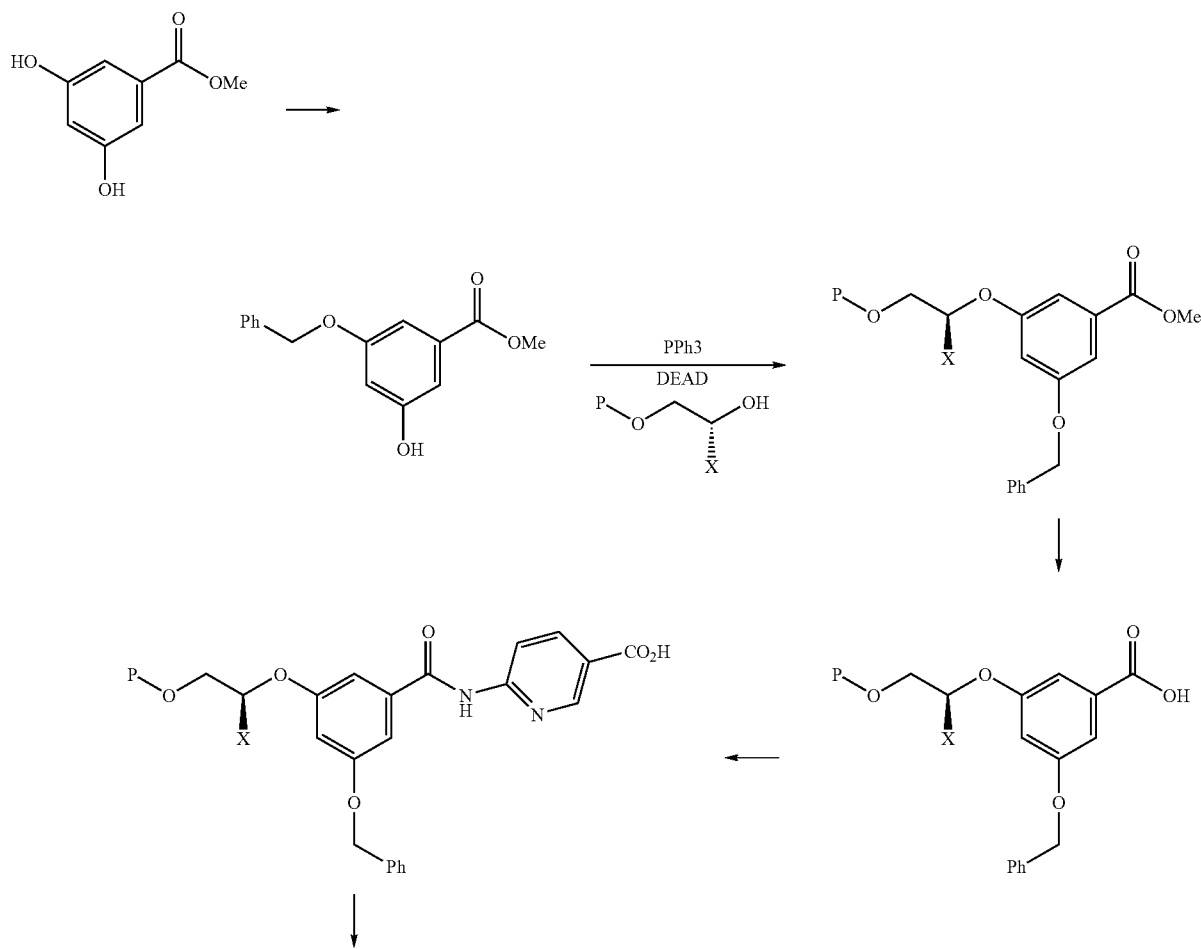

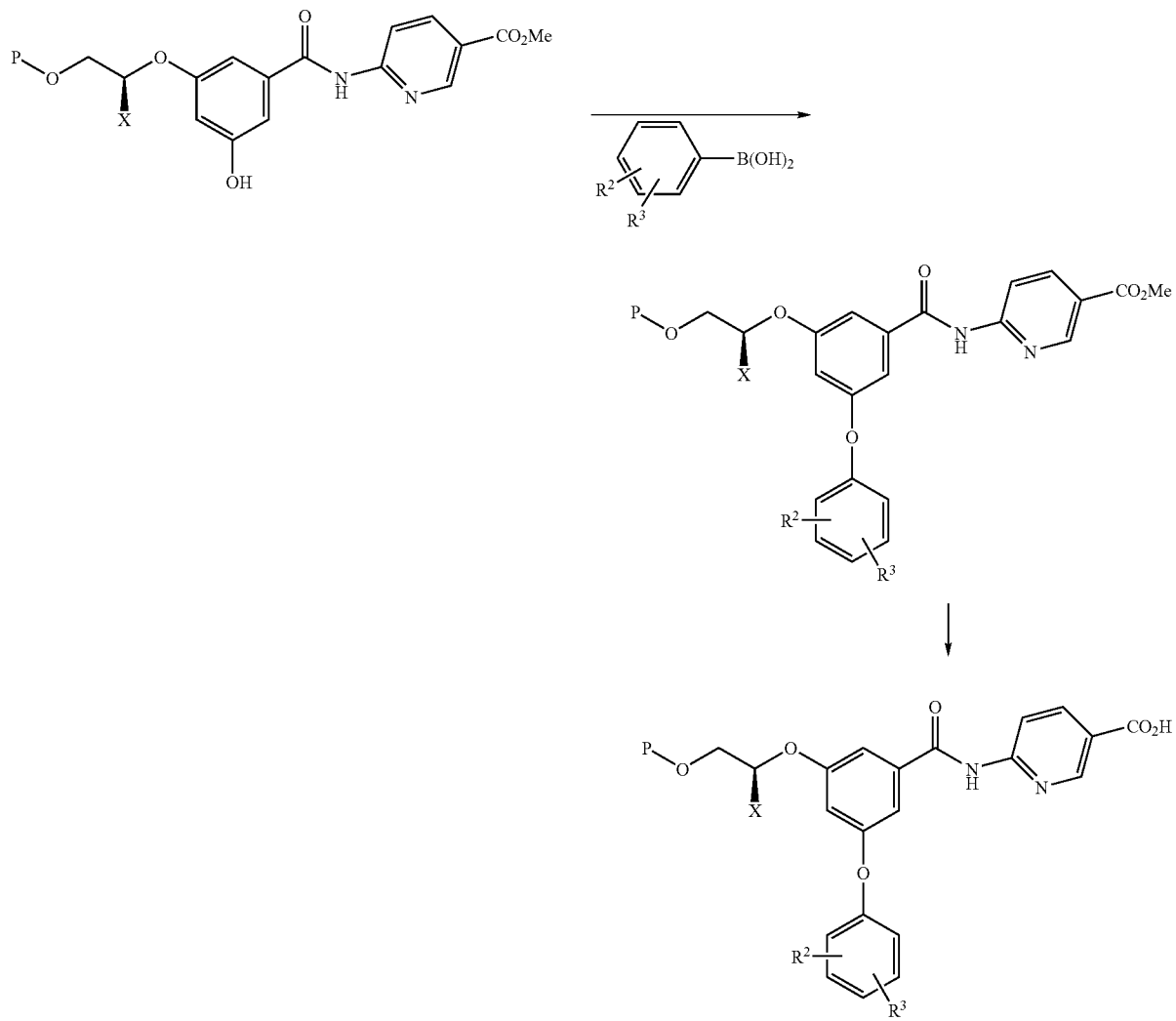

The starting material for both of these synthetic routes is methyl(3,5-dihydroxy)benzoate. The order of attaching the various substituents around the phenyl ring has varied, but in both routes illustrated, it has been necessary to use protecting groups (benzyl in Schemes 1 and 2) during the synthetic sequence in order to differentiate between the two hydroxy groups in the starting material. This inevitably introduces extra synthetic steps with the consequent implications for increased cost per unit weight of final product and increased waste and environmental impact, if the product were to be manufactured on significant scale.

Concurrently, compounds with a similar general formula have been published (WO 2004/076420). A route used to these compounds is illustrated in Scheme 3.

Scheme 3

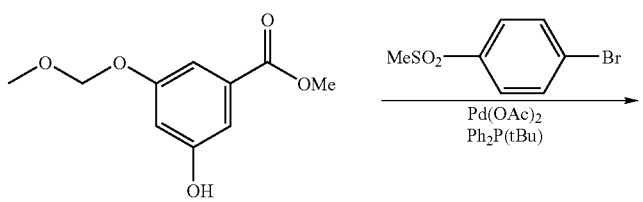

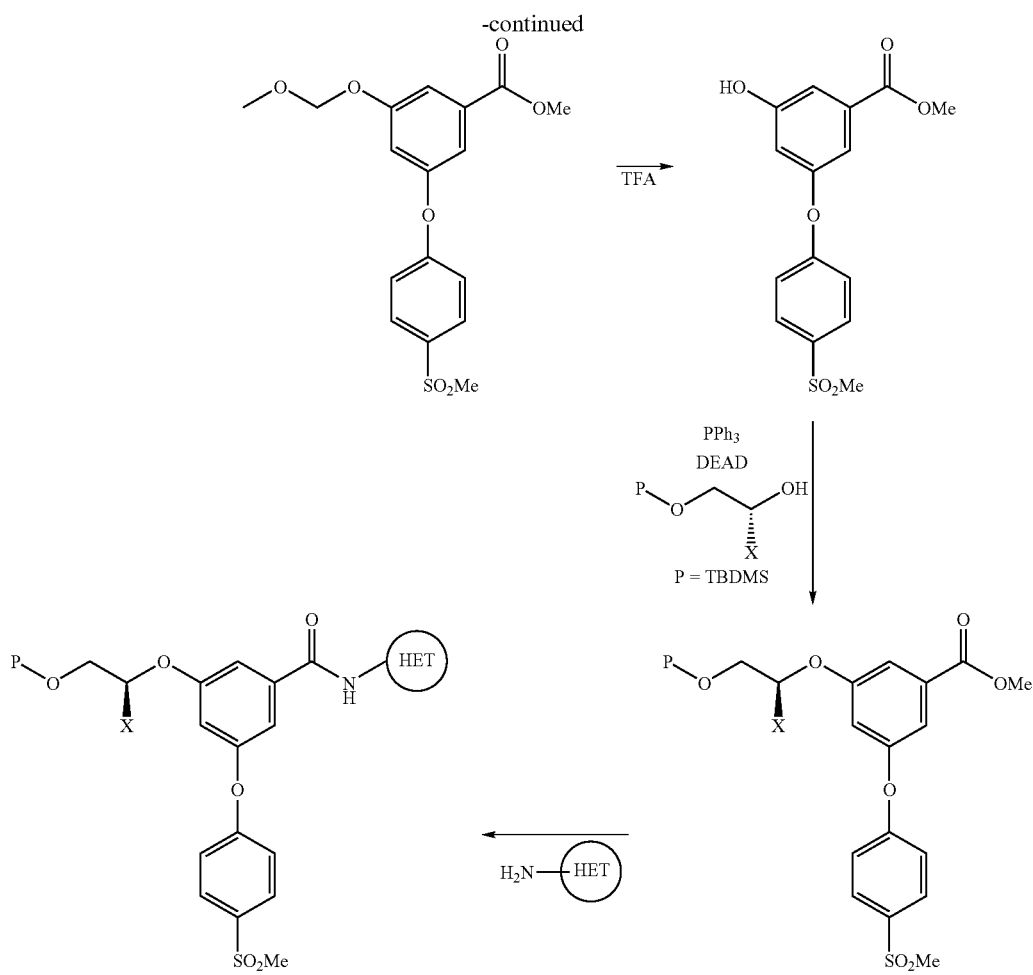

However, as shown above, a methoxymethyl protecting group is still utilised in this route.

In order for such compounds to be useful commercially, there is a need to develop one or more short, efficient synthetic routes. We have found that the problems associated with the previous routes as described above can be overcome by using halo substituted starting materials and optionally carboxylic acid precursors instead of an acid or ester as used above. This not only results in a short, efficient route, but avoids the need for several protecting groups.

Additionally, certain aspects of the process of the present invention avoid the need for use of Mitsunobu conditions (PPh$_3$, diethylazodicarboxylate (DEAD)) which give undesirable by-products (P(O)Ph$_3$) and use starting materials with a potential explosion hazard (DEAD). Additionally, certain aspects of the process of the present invention avoid the need for use of any heavy metals catalysts, thus minimising undesirable waste and minimising the potential for residue in the product.

According to a first aspect of the invention, there is provided a process for making a compound of formula (I),

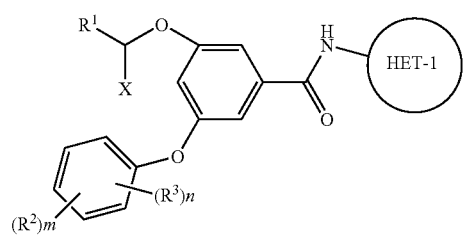

said process comprising
a) reaction of a compound of formula (II)

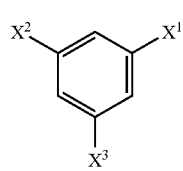

wherein $X^1$ is carboxyl or precursor thereof, $X^2$ is F and $X^3$ is selected from F, Br and OH; with:

i) a compound of formula (III) by nucleophilic aromatic substitution of X² using a suitable base in a suitable solvent,

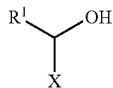

wherein X is as defined for formula (I) below and R¹ is selected from methyl, methoxymethyl and hydroxymethyl (or a protected version thereof); and ii) a compound of formula (IV) by nucleophilic aromatic substitution using a suitable base in a suitable solvent, or, when X³ is Br, under conditions suitable for an Ullman ether reaction,

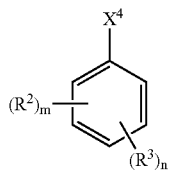

wherein $R^2$, $R^3$, m and n are as defined for formula (I) and $X^4$ is OH when $X^3$ is F or Br, and $X^4$ is a leaving group when $X^3$ is OH;

b) where necessary, conversion of $X^1$ into a carboxylic acid; and c) coupling of the carboxylic acid group to a compound of formula (V);

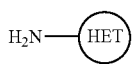

and thereafter if necessary:
i) converting a compound of formula (I) into another compound of formula (I);
ii) where $R^1$ is a protected version of hydroxymethyl, removal of the protecting group;
iii) forming a pro-drug; and/or
iv) forming a pharmaceutically acceptable salt;
wherein in a compound of formula (I):
$R^1$ is hydroxymethyl, methoxymethyl or methyl;
X is methyl or ethyl;
$R^2$ is selected from $-C(O)NR^4R^5$, $-SO_2NR^4R^5$, $-S(O)_pR^4$ and HET-2;
HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;
HET-2 is a 4-, 5- or 6-membered, C- or N-linked heterocyclyl ring containing 1, 2, 3 or 4 heteroatoms independently selected from O, N and S, wherein a $-CH_2-$ group can optionally be replaced by a $-C(O)-$, and wherein a sulphur atom in the heterocyclic ring may optionally be oxidised to a S(O) or S(O)₂ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl [optionally substituted by 1 or 2 substituents independently selected from HET-2, $-OR^5$, $-SO_2R^5$, (3-6C)cycloalkyl (optionally substituted with 1 group selected from $R^7$) and $-C(O)NR^5R^5$], (3-6C)cycloalkyl (optionally substituted with 1 group selected from $R^7$ and HET-2;

$R^5$ is hydrogen or (1-4C)alkyl;

or $R^4$ and $R^5$ together with the nitrogen atom to which they are attached may form a heterocyclyl ring system as defined by HET-3;

$R^6$ is independently selected from (1-4C)alkyl, halo, hydroxy (1-4C)alkyl, (1-4C)alkoxy(1-4C)alkyl, (1-4C)alkylS(O)$_p$ (1-4C)alkyl, amino(1-4C)alkyl, (1-4C)alkylamino(1-4C) alkyl, di(1-4C)alkylamino(1-4C)alkyl and HET-4;

or, when HET-1 is 2-pyridyl, $R^6$ may additionally be carboxy;

$R^7$ is selected from $-OR^5$, (1-4C)alkyl, $-C(O)(1-4C)$alkyl, $-C(O)NR^4R^5$, (1-4C)alkoxy(1-4C)alkyl, hydroxy(1-4C) alkyl and $-S(O)_pR^5$;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a $-CH_2-$ group can optionally be replaced by a $-C(O)-$ and wherein a sulphur atom in the ring may optionally be oxidised to a S(O) or S(O)₂ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a $-CH_2-$ group can optionally be replaced by a $-C(O)-$ group and wherein a sulphur atom in the ring may optionally be oxidised to a S(O) or S(O)₂ group; which ring is optionally substituted on an available carbon or nitrogen atom by 1 or 2 substituents independently selected from $R^8$; or HET-3 is an 6-10 membered bicyclic saturated or partially unsaturated heterocyclyl ring, optionally containing 1 further nitrogen atom (in addition to the linking N atom), wherein a $-CH_2-$ group can optionally be replaced by a $-C(O)-$; which ring is optionally substituted on an available carbon or nitrogen atom by 1 substituent selected from hydroxy and $R^3$;

$R^8$ is selected from $-OR^5$, (1-4C)alkyl, $-C(O)(1-4C)$alkyl, $-C(O)NR^4R^5$, (1-4C)alkylamino, di(1-4C)alkylamino, HET-3 (wherein said ring is unsubstituted), (1-4C)alkoxy (1-4C)alkyl, hydroxy(1-4C)alkyl and $-S(O)pR^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1; and n is 0, 1 or 2;

provided that when m is 0, then n is 1 or 2.

It will be understood that steps a)i) and ii) may be carried out in either order, with the preferred order depending on the nature of the substituents $R^1$ to $R^3$ and $X^1$ to $X^4$, as shown in Scheme 4:

Scheme 4

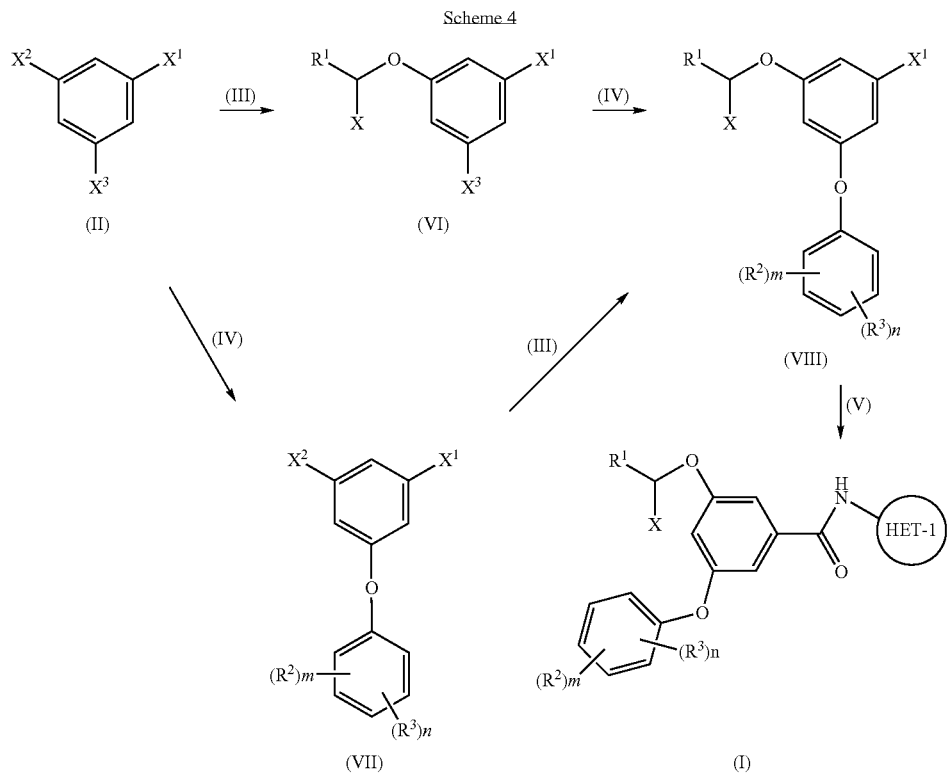

Certain compounds of formula (VI), (VII) and (VIII) are novel and form separate independent aspects of the invention.

Particular compounds of formula (VI) where $X^1$ is a precursor to a carboxylic acid include any one or more of:
3-bromo-5-isopropoxy-benzonitrile;
3-bromo-5-(2-methoxy-1-methylethoxy)benzonitrile;
3-bromo-5-(2-tert-butoxy-1-methylethoxy)benzonitrile;
3-bromo-5-(2-benzyloxy-1-methylethoxy)benzonitrile;
3-bromo-5-(2-(triphenylmethyl)oxy-1-methylethoxy)benzonitrile;
3-bromo-5-(2-tetrahydropyranyloxy-1-methylethoxy)benzonitrile; and
3-bromo-5-(2-allyloxy-1-methylethoxy)benzonitrile.

Further particular compounds of formula (VI) where $X^1$ is a precursor to a carboxylic acid include any one or more of:
3-bromo-5-(2-methoxy-1-ethylethoxy)benzonitrile;
3-bromo-5-(2-tert-butoxy-1-ethylethoxy)benzonitrile;
3-bromo-5-(2-benzyloxy-1-ethylethoxy)benzonitrile;
3-bromo-5-(2-(triphenylmethyl)oxy-1-ethylethoxy)benzonitrile;
3-bromo-5-(2-tetrahydropyranyloxy-1-ethylethoxy)benzonitrile; and
3-bromo-5-(2-allyloxy-1-ethylethoxy)benzonitrile.

Particular compounds of formula (VI) where $X^1$ is a carboxylic acid include any one or more of:
3-bromo-5-isopropoxy-benzoic acid;
3-bromo-5-(2-methoxy-1-methylethoxy)benzoic acid;
3-bromo-5-(2-tert-butoxy-1-methylethoxy)benzoic acid;
3-bromo-5-(2-benzyloxy-1-methylethoxy)benzoic acid;
3-bromo-5-(2-(triphenylmethyl)oxy-1-methylethoxy)benzoic acid;
3-bromo-5-(2-tetrahydropyranyloxy-1-methylethoxy)benzoic acid; and
3-bromo-5-(2-allyloxy-1-methylethoxy)benzoic acid.

Further particular compounds of formula (VI) where $X^1$ is a carboxylic acid include any one or more of:
3-bromo-5-(2-methoxy-1-ethylethoxy)benzoic acid;
3-bromo-5-(2-tert-butoxy-1-ethylethoxy)benzoic acid;
3-bromo-5-(2-benzyloxy-1-ethylethoxy)benzoic acid;
3-bromo-5-(2-(triphenylmethyl)oxy-1-ethylethoxy)benzoic acid;
3-bromo-5-(2-tetrahydropyranyloxy-1-ethylethoxy)benzoic acid; and
3-bromo-5-(2-allyloxy-1-ethylethoxy)benzoic acid.

Further particular compounds of formula (VI) include the above particular compounds as single enantiomers, particularly the (1S) enantiomers.

A particular compound of formula (VII) is 3-fluoro-5-[4-(methanesulfonyl)phenoxy]benzonitrile.

Particular compounds of formula (VIII) are:
3-[(1S)-2-methoxy-1-methylethoxy]-5-[4-(methylsulfonyl)phenoxy]benzonitrile [and the racemic version which is also written as 3-(4-methanesulfonyl-phenoxy)-5-(2-methoxy-1-methyl-ethoxy)benzonitrile];
3-[(1S)-2-methoxy-1-methylethoxy]-5-[4-(methylsulfonyl)phenoxy]benzoic acid [and the racemic version which is also written as 3-(4-methanesulfonyl-phenoxy)-5-(2-methoxy-1-methyl-ethoxy)benzoic acid];
3-[(1S)-2-tert-butoxy-1-methylethoxy]-5-[4-(methylsulfonyl)phenoxy]benzonitrile; and
3-[(1S)-2-tert-butoxy-1-methylethoxy]-5-[4-(methylsulfonyl)phenoxy]benzoic acid.

Further particular compounds of the formula (VIII) include any one or more of:

3-[isopropoxy]-5-[4-(methylsulfonyl)phenoxy]benzonitrile;
3-[isopropoxy]-5-[4-(methylsulfonyl)phenoxy]benzoic acid;
3-[(1S)-2-benzyloxy-1-methylethoxy]-5-[4-(methylsulfonyl)phenoxy]benzonitrile;
3-[(1S)-2-benzyloxy-1-methylethoxy]-5-[4-(methylsulfonyl)phenoxy]benzoic acid;
3-[(1S)-2-triphenylmethyloxy-1-methylethoxy]-5-[4-(methylsulfonyl)phenoxy]benzonitrile;
3-[(1S)-2-triphenylmethyloxy-1-methylethoxy]-5-[4-(methylsulfonyl)phenoxy]benzoic acid;
3-[(1S)-2-tetrahydropyranyloxy-1-methylethoxy]-5-[4-(methylsulfonyl)phenoxy]benzonitrile;
3-[(1S)-2-tetrahydropyranyloxy-1-methylethoxy]-5-[4-(methylsulfonyl)phenoxy]benzoic acid;
3-[(1S)-2-allyloxy-1-methylethoxy]-5-[4-(methylsulfonyl)phenoxy]benzonitrile; and
3-[(1S)-2-allyloxy-1-methylethoxy]-5-[4-(methylsulfonyl)phenoxy]benzoic acid.

A further particular compound of the formula (VIII) is 3-[hydroxy]-5-[4-(methylsulfonyl)phenoxy]benzoic acid.

A particular compound of formula (I) (protected version) is 3-[(1S)-2-tert-butoxy-1-methylethoxy]-N-(1-methyl-1H-pyrazol-3-yl)-5-[4-(methylsulfonyl)phenoxy]benzamide.

Suitable values for protecting groups used to protect a hydroxymethyl group in $R^1$ are any of those known in the art for protecting primary alcohol (see for example "Protective groups in Organic Chemistry" $2^{nd}$ Edition, T W Greene and P G M Wuts, 1991). Compounds of formula (II) containing such protecting groups can be made by methods known in the art from the commercially available propanediol starting materials, for example when X is methyl:

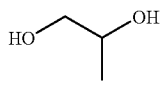

Further suitable values for protecting groups used to protect a hydroxymethyl group in $R^1$ are t-butyl, benzyl, trityl (triphenylmethyl) and tetrahydropyran-2-yl; such that the preferred compounds of formula (III) are:

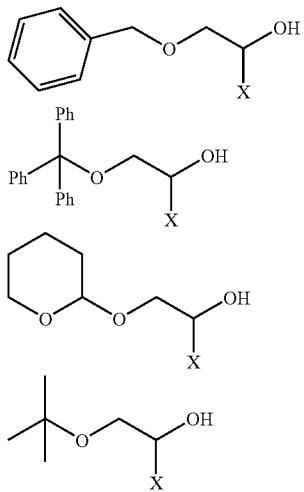

A further suitable protecting group is an allyl ether.
In one aspect, the tert-butyl ether:

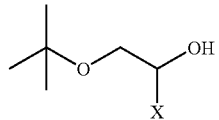

is a preferred protecting group.

These protecting groups may be removed at a convenient moment in the synthetic sequence by methods known in the art. For example, a benzyl group may be removed by hydrogenation. A trityl group or a tert-butyl group may be removed by treatment with acid. Suitable acids or acidic conditions for removal of a tert-butyl group are, for example, treatment with hydrochloric acid in methanol, or treatment with amberlyst resin, or treatment with formic acid.

Suitable values for $X^1$ as a carboxylic acid precursor are —$CO_2$(1-4C)alkyl, —CHO, —$CH_2$OP (where P is a suitable protecting group), cyano, trifluoromethyl, methyl and halo.

Further suitable values are —$CO_2$Et, cyano and trifluoromethyl.

Preferred values are cyano and trifluoromethyl, particularly cyano.

Suitable conditions for the process steps a) to c) are given below:

Process step a)i) Suitable solvents for nucleophilic aromatic substitution reactions are known in the art (see for example Advanced Organic Chemistry, M B Smith & J March (eds), 2001, 5th Edition, Chapter 13, pg 850); generally a polar aprotic solvent is suitable, for example dimethylformamide (DMF), N-methylpyrrolidinone (NMP), dimethylsulfoxide (DMSO) or dimethylacetamide (DMA). Suitable bases are any of those known in the art for such reactions and include, for example, inorganic bases such as potassium carbonate, sodium carbonate, sodium hydride and organic bases such as lithium hexamethyldisilazide.

More suitably the solvent is DMF and the base is potassium carbonate.

Process step a) ii) Suitable conditions for this reaction when $X^3$ is F and $X^4$ is OH, are generally those described above for step a)i). More suitably, the solvent is DMF and the base is lithium hexamethyldisilazide.

When $X^3$=Br, the reaction is an Ullman reaction; such reactions and the conditions required to carry them out are well known in the art (see for example K Kunz, U Scholz, D Ganzer, *Synlett*, 2003, 2428-2439, G Mann, C Incarvito, A L Rheingold & J Hartwig, *J. Am. Chem. Soc.,* 1999, 121, 3224-3225 and A Aranyos, D W Old, A Kiyomori, J P Wolfe, J P Sadighi & S L Buckwald, *J. Am. Chem. Soc.,* 1999, 121, 4369-4378.

Generally, suitable conditions are use of a high boiling solvent for example toluene, 1,4-dioxane or DMSO, using a copper or palladium catalyst, for example copper, copper (I) chloride, copper (I) bromide, copper (I) iodide, copper (II) chloride, copper (II) bromide, copper (II) iodide, copper (II) oxide, palladium (II) acetate or bisdibenzylideneacetone palladium (0), a ligand for the catalyst for example 1,10-phenanthronine, neocuprine, a 1,3-diketone, racemic-2-(di-t-butylphsophino)-1,1'-binaphthyl, 2-(di-t-butylphosphino)biphenyl or 1,1'-bis(di-t-butylphosphino)ferrocene, and a base for example, inorganic bases such as potassium carbonate, cesium carbonate and organic bases such as sodium tert-butoxide to deprotonate the phenol.

For example the reaction may be conducted in NMP, using copper (I) chloride as catalyst, 2,2,6,6-tetramethyl-3,5-heptanedione as ligand and cesium carbonate as base.

When $X^3$=OH, and $X^4$ is a leaving group, the nucleophilic aromatic substitution reaction is similarly carried out in a suitable solvent (normally a polar aprotic) such as DMF, NMP, DMSO or DMA using a base such as potassium carbonate, sodium carbonate or sodium hydride to deprotonate the phenol. Suitable values for $X^4$ as a leaving group, are for example halo, mesylate and tosylate. More suitably, $X^4$ is a halo, preferably fluoro.

Process step b) Suitable conditions, where necessary, for conversion of $X^1$ to a carboxylic acid are as follows:

$X^1$ is —CO$_2$(1-4C)alkyl: hydrolysis in aqueous acid or base;
$X^1$ is —CHO: oxidation using for example silver (I) oxide, sodium tungstate/hydrogen peroxide;
$X^1$ is —CH$_2$OP: deprotection (conditions vary depending on protecting group use and are well known in the art) and oxidation using, for example, manganese (IV) oxide, sodium tungstate/hydrogen peroxide,
$X^1$ is CN: hydrolysis using aqueous or organic solution of an acid or base (for example aqueous hydrochloric acid or aqueous sodium hydroxide solution)
$X^1$ is trifluoromethyl: strong acid for example concentrated sulfuric acid
$X^1$ is methyl: oxidation using for example potassium permanganate
$X^1$ is halogen: carboxylation, typically using a strong base (for example n-butyl lithium) and carbon dioxide It will be understood that alternatives to the above illustrative conditions, which are well known in the art, may be used, particularly where the skilled person would understand that alternatives would be preferred due to the nature of the substituents present in the compound.

Preferably, $X^1$=CN and the reaction is carried out using sodium hydroxide as the base in 10% water in ethanol as the solvent.

It will be understood that the resulting acid may be isolated as the free acid, or as a salt of the acid, depending on the conditions used. A salt may be used directly in the next step of the process, or may be converted (for example in situ) to the free acid, using conditions well known in the art.

Particular salts of compounds of formula (VIII) where $X^1$ is a carboxylic acid may be alkali metal salts, alkaline earth metal salts or salts with organic bases, such as amines. Particular examples are the morpholine and tert-butylamine salts of 3-[(1S)-2-tert-butoxy-1-methylethoxy]-5-[4-(methylsulfonyl)phenoxy]benzoic acid, more particularly the tert-butylamine salt.

Process step c) suitable conditions for coupling a carboxylic acid derivative to the heterocyclic amine derivative of formula (V) are well known in the art, for example, (i) using an appropriate coupling reaction, such as a carbodiimide coupling reaction performed with 1-(3-dimethylaminopropyl)-3-ethylcarbodiimide hydrochloride (EDAC) in the presence of dimethylaminopyridine (4-DMAP) in a suitable solvent such as DCM, chloroform or DMF at room temperature; or alternatively with carbonyldiimidazole (CDI) in a suitable solvent such as THF at room temperature; or (ii) reaction in which the carboxylic group is activated to an acid chloride by reaction with oxalyl chloride in the presence of a suitable solvent such as DCM, and where necessary catalytic amount of DMF. The acid chloride can then be reacted with a compound of formula (V) in the presence of a base, such as triethylamine or pyridine, in a suitable solvent such as DCM or pyridine at a temperature between 0° C. and 80° C.

Preferred conditions for process c) are carbonyldiimidazole (CDI) in a suitable solvent such as THF at room temperature.

For examples of protecting groups known in the art (as well as means of formation and eventual deprotection), see T. W. Greene and P. G. M. Wuts, "Protective Groups in Organic Synthesis", Third Edition, John Wiley & Sons, New York, 1999.

In a further aspect of the invention, there is provided each individual step of the process described above; that is each of the conversions of compounds of formula (II) to (VI), (II) to (VII), (VI) to (VIII) and (VII) to (VIII) is provided as an individual independent aspect of the invention.

In an alternative aspect of the invention, when $X^1$ is CN, step b) comprises a partial hydrolysis of CN to —CONH$_2$, and step c) then comprises coupling to a halo-heterocyclic derivative of formula (IX), wherein halo is suitably chloro, bromo or iodo; using palladium or nickel catalysis.

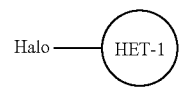

(IX)

In a further alternative aspect of the invention, $X^2$ is hydroxy, and step a)i) is carried out using a compound of formula (X):

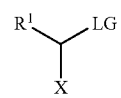

(X)

where X is as hereinbefore defined for a compound of formula (III), and LG is a leaving group such as halo, mesylate or tosylate. It will be appreciated that this nucleophilic substitution reaction causes inversion of the stereochemistry at the chiral centre present in the compound of formula (X). Suitable conditions for such reactions include the use of polar aprotic solvents such as DMF, NMP, DMSO or DMA, and a base, for example an inorganic base such as potassium carbonate, sodium carbonate or sodium hydride. For general information on such S$_N^2$ reactions, see for example Advanced Organic Chemistry, M B Smith & J March (eds), 2001, 5th Edition, Chapter 10, p 389.

In one aspect of the invention, $X^3$ is selected from F and OH. In a further aspect, $X^3$ is F.

In one aspect the compound of formula (II) is 3-hydroxy-5-trifluoromethyl-fluorobenzene.

In another aspect the compound of formula (II) is 3-fluoro-5-cyano-bromobenzene.

In a further aspect the compound of formula (II) is 3,5-difluorobenzonitrile.

In another aspect, step a)i) is carried out before a)ii); that is the sequence as shown in Scheme 4 is (II)→(VI)→(VIII), as illustrated below:

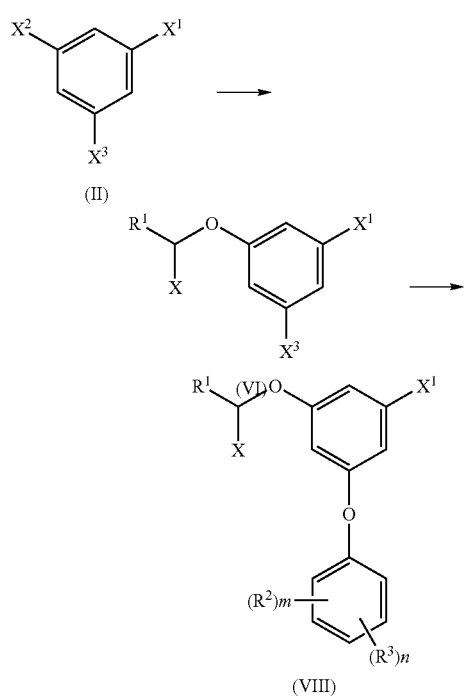

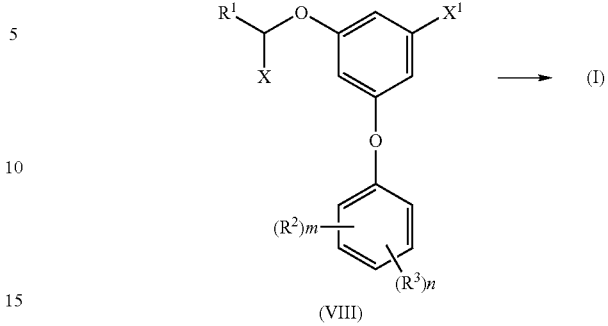

In another aspect, step a)ii) is carried out before a)i); that is the sequence as shown in Scheme 4 is (II)→(VII)→(VIII), as illustrated below:

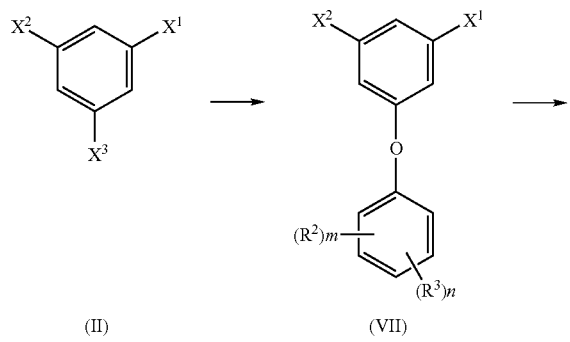

In a preferred aspect of the invention, the compound of formula (II) is 3,5-difluorobenzonitrile and step a)ii) is carried out before a)i).

In a further aspect of the invention, there is provided a process for making a compound of formula (Ib) [illustrated in Scheme 5], said process comprising:

i) reaction of difluorobenzonitrile (IIa) with 4-methanesulfonylphenol to give the compound of formula (VIIa);

(ii) reaction of the compound of formula (VIIa) with the compound of formula (IIIa) (wherein $R^{1a}$ is methoxymethyl, hydroxymethyl or a protected version thereof) to give the compound of formula (VIIIa);

(iii) hydrolysis of the nitrile to give the compound of formula (VIIIb); reaction with a heterocyclic amine to give the compound of formula (Ib);

and thereafter if necessary:

i) converting a compound of formula (Ib) into another compound of formula (Ib);

ii) where $R^{1a}$ is a protected version of hydroxymethyl, removal of the protecting group;

iii) forming a pro-drug; and/or iv) forming a pharmaceutically acceptable salt;

Scheme 5

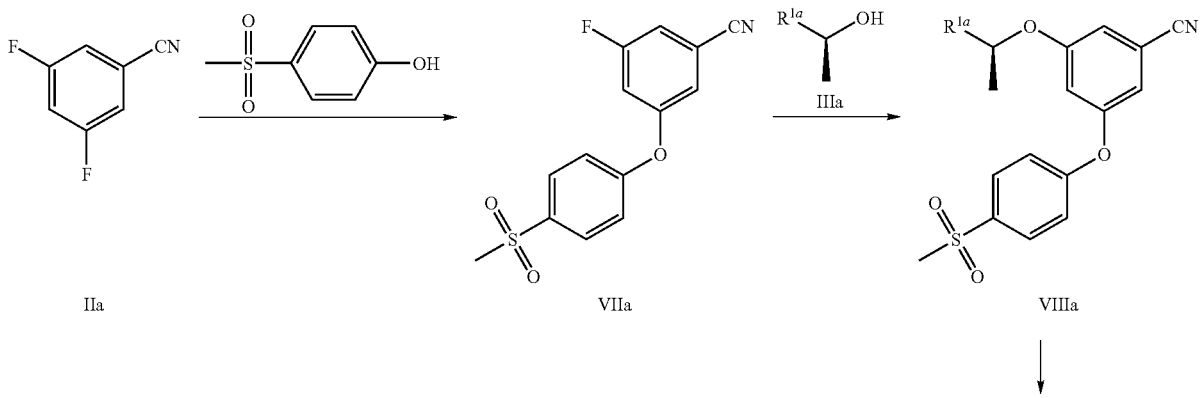

-continued

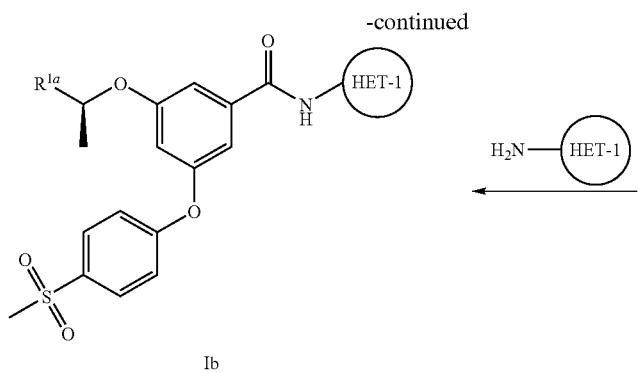

Ib

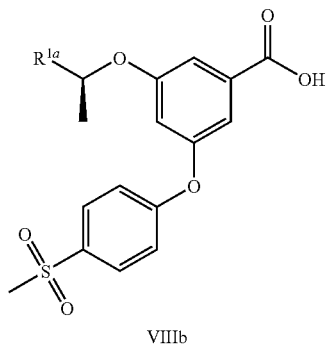

VIIIb

In this aspect of the invention suitably:

$R^{1a}$ is methoxymethyl or tertbutoxymethyl (as a protected version of hydroxymethyl);

HET-1 is pyrazolyl, optionally substituted with (1-4C) alkyl; and/or the compound (VIIb) is isolated as a salt;

In a further aspect of the invention there is provided a process as shown in Scheme 5, wherein the compound of formula (Ib), wherein $R^{1a}$ is methoxymethyl or tertbutoxymethyl, is subsequently converted to a compound of formula (Ib) wherein $R^{1a}$ is hydroxymethyl.

In one embodiment of this aspect, the compound of formula (VIIIb) is converted to the compound of formula (Ib) (wherein $R^{1a}$ is hydroxymethyl) without isolation of the intermediate compound of formula (Ib) (wherein $R^{1a}$ is methoxymethyl or tertbutoxymethyl).

Examples of conversions of a compound of Formula (I) into another compound of Formula (I), well known to those skilled in the art, include functional group interconversions such as hydrolysis, oxidation or reduction, and/or further functionalisation by standard reactions such as amide or metal-catalysed coupling, or nucleophilic displacement reactions.

It will be appreciated that, under some conditions for the conversion of one compound of formula (I) or (Ib) into another compound of formula (I) or (Ib), or under conditions for removal of a protecting group from a protected version of a compound of formula (I) or (Ib), a salt may be formed. This salt may then be used as the final desired compound, or may be converted to the free form of the compound of formula (I) or (Ib), or may be converted to an alternative salt form, as required, by methods known in the art. Such a process is illustrated in the accompanying examples.

It will be appreciated that some of the intermediates described herein may themselves have activity as activators of GLK and are thus presented as an independent aspect of the invention. It will further be appreciated that certain intermediates described herein may also be metabolites formed in vivo by dosing of a compound of formula (I) or (Ib) to a warm-blooded animal, such as a human.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms. For the avoidance of doubt, reference to the group HET-1 containing a nitrogen in the 2-position, is intended to refer to the 2-position relative to the amide nitrogen atom to which the group is attached.

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

It will be understood that HET-2 can be a saturated, or partially or fully unsaturated ring.

Suitable examples of HET-2 include azetidinyl, furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, morpholino, morpholinyl, piperidinyl, piperazinyl, morpholinyl, thiomorpholinyl, pyrrolyl, pyrrolidinyl, pyrrolidonyl, 2,5-dioxopyrrolidinyl, 1,1-dioxotetrahydrothienyl, 2-oxoimidazolidinyl, 2,4-dioxoimidazolidinyl, 2-oxo-1,3,4-(4-triazolinyl), 2-oxazolidinonyl, 2-oxotetrahydrofuranyl, tetrahydrofuranyl, tetrahydropyranyl, 1,1-dioxothiomorpholino, 1,3-dioxolanyl, 1,2,4-triazolyl, 1,2,3-triazolyl, pyranyl, and 4-pyridonyl.

It will be understood that HET-2 may be linked by any appropriate available C or N atom, therefore for example, for HET-2 as "imidazolyl" includes 1-, 2-, 4- and 5-imidazolyl.

Suitable examples of HET-3 as a 4-6 membered saturated or partially unsaturated heterocyclic ring are morpholino, piperidinyl, piperazinyl, pyrrolidinyl and azetidinyl.

A suitable example of HET-3 as a 7-membered saturated or partially unsaturated heterocyclic ring is homopiperazinyl, homo-morpholino, homo-thiomorpholino (and versions thereof wherein the sulfur is oxidised to an SO or $S(O)_2$ group) and homo-piperidinyl.

Suitable examples of HET-3 as an 6-10 membered bicyclic heterocyclic ring are bicyclic saturated or partially unsaturated heterocyclyl ring such as those illustrated by the structures shown below (wherein the dotted line indicates the point of attachment to the rest of the molecule):

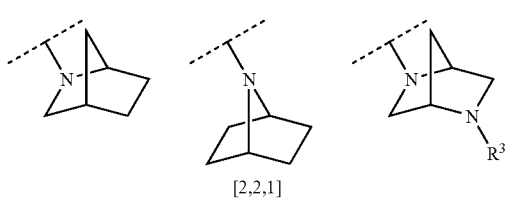

[2,2,1]

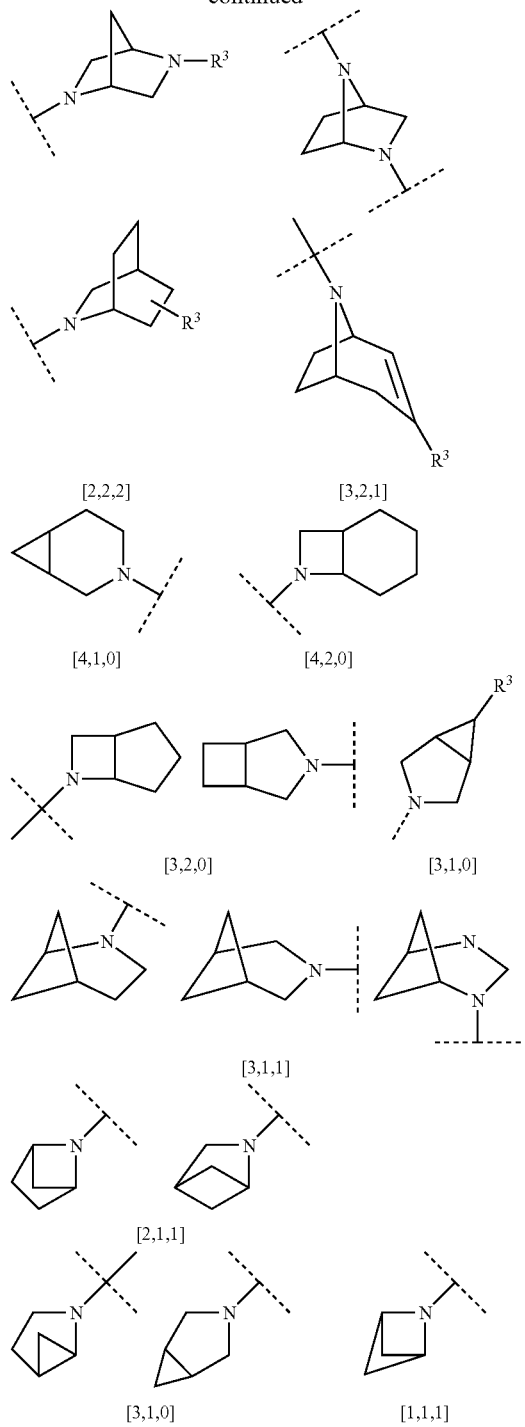

Suitable examples of HET-4 are furyl, pyrrolyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl and triazolyl.

It will be appreciated that, where definitions of heterocylyl groups HET-1 to HET-4 encompass heteroaryl rings which may be substituted on nitrogen, such substitution may not result in charged quaternary nitrogen atoms. It will be appreciated that the definitions of HET-1 to HET-4 are not intended to include any O—O, O—S or S—S bonds. It will be appreciated that the definitions of HET-1 to HET-4 are not intended to include unstable structures.

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; examples of (1-4C)alkylS(O)$_p$(1-4C)alkyl include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of amino(1-4C)alkyl include aminomethyl, amino ethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of (1-4C)alkylamino include methylamino, ethylamino, propylamino, isopropylamino, butylamino and tert-butylamino; examples of di(1-4C)alkylamino include dimethylamino, methyl(ethyl)amino, diethylamino, dipropylamino, di-isopropylamino and dibutylamino; examples of —C(O)(1-4C)alkyl include methylcarbonyl, ethylcarbonyl, propylcarbonyl and tert-butyl carbonyl.

In a further aspect of the invention, there is provided a compound of formula (I) as hereinbefore defined wherein:
R$^1$ is hydroxymethyl;
X is methyl or ethyl, preferably methyl;
HET-1 is pyrazolyl, thiazolyl or thiadiazolyl, and HET-1 is optionally substituted with methyl or ethyl;
R$^3$ is fluoro or chloro;
m is 1 and n is 0 or 1;
R$^2$ is selected from methylsulfonyl, azetidinylcarbonyl, dimethylaminocarbonyl, ethylsulfonyl, dimethylaminosulfonyl and pyrrolidinylcarbonyl;

or a salt, pro-drug or solvate thereof.

In a further aspect of the invention, there is provided a compound of formula (I) as hereinbefore defined wherein:
R$^1$ is hydroxymethyl;
X is methyl or ethyl;
HET-1 is pyrazolyl, thiazolyl or thiadiazolyl, and HET-1 is optionally substituted with methyl or ethyl;
R$^3$ is fluoro or chloro;
m is 1 and n is 0 or 1;
R$^2$ is selected from azetidinylcarbonyl and pyrrolidinylcarbonyl;

or a salt, pro-drug or solvate thereof.

In a further aspect of the invention, there is provided a compound of formula (I) as hereinbefore defined wherein:
R$^1$ is hydroxymethyl;
X is methyl or ethyl, preferably methyl;
HET-1 is pyrazolyl, thiazolyl or thiadiazolyl, and HET-1 is optionally substituted with methyl or ethyl;
R$^3$ is fluoro or chloro;
m is 1 and n is 0 or 1;
R$^2$ is methylsulfonyl;

or a salt, pro-drug or solvate thereof.

In a further aspect of the invention, the compound of formula (I) is a compound of formula (Ia)

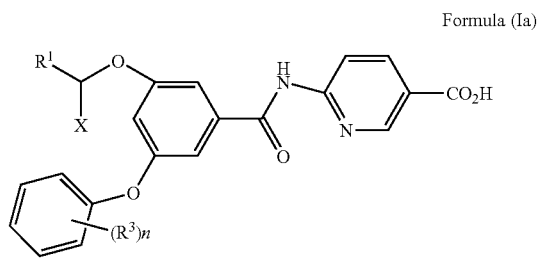

Formula (Ia)

wherein:
R$^3$ is selected from fluoro, chloro, C$_{1-3}$alkyl and C$_{1-3}$alkoxy;
R$^1$ is selected from methyl and methoxymethyl;
n is 0, 1 or 2;
X is methyl;

or a salt, pro-drug or solvate thereof.

In a further aspect of the invention there is provided a compound of formula (I) obtainable by the processes of the invention. In a particular embodiment of this aspect, said compound of formula (I) is a compound of formula (Ib) and is:

3-[(1S)-2-hydroxy-1-methylethoxy]-N-(1-methyl-1H-pyrazol-3-yl)-5-[4-(methylsulfonyl)phenoxy]benzamide. In a further particular embodiment of this aspect, said compound of formula (I) is a compound of formula (Ib) and is:

3-[(1S)-2-methoxy-1-methylethoxy]-N-(1-methyl-1H-pyrazol-3-yl)-5-[4-(methylsulfonyl)phenoxy]benzamide. In a further particular embodiment of this aspect, said compound of formula (I) is a compound of formula (Ib) and is:

3-[(1S)-2-tert-butoxy-1-methylethoxy]-N-(1-methyl-1H-pyrazol-3-yl)-5-[4-(methylsulfonyl)phenoxy]benzamide.

The compounds made by the process of the invention are useful as activators of glucokinase (GLK). This activity may be demonstrated by test methods known in the art, for example those given in our patent application WO 03/015774, WO2005/080359 and WO2005/080360. See also Brocklehurst et al, Diabetes 2004, 53, 535-541.

It will be appreciated that methods for, for example purification, of the compounds in the Examples below are illustrative and alternatives may be used where the skilled person would deem them appropriate.

The invention will now be illustrated by the following Examples, in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis; and (vi) Biotage cartridges refer to pre-packed silica cartridges (from 40 g up to 400 g), eluted using a biotage pump and fraction collector system; Biotage UK Ltd, Hertford, Herts, UK.

ABBREVIATIONS

DCM dichloromethane
DMSO dimethyl sulphoxide
DMF dimethylformamide
HPLC high pressure liquid chromatography
LCMS liquid chromatography/mass spectroscopy
NMR nuclear magnetic resonance spectroscopy
$CDCl_3$ deuterochloroform
NaHMDS sodium hexamethyldisilazide
MTBE methyltert-butyl ether
THF tetrahydrofuran
TMSI trimethylsilyliodide
NMP N-methylpyrrolidone
TFA trifluoroacetic acid
HATU O-(7-Azabenzotriazol-1-yl)-N,N,N',N'-tetramethyluronium hexofluorophosphate

EXAMPLE 1

Starting from Difluorobenzonitrile

Preparation of 3-{[(1S)-1-(Hydroxymethyl)ethyl]oxy}-N-(1-methyl-1H-pyrazol-3-yl)-5-[4-(methylsulfonyl)phenoxy]benzamide

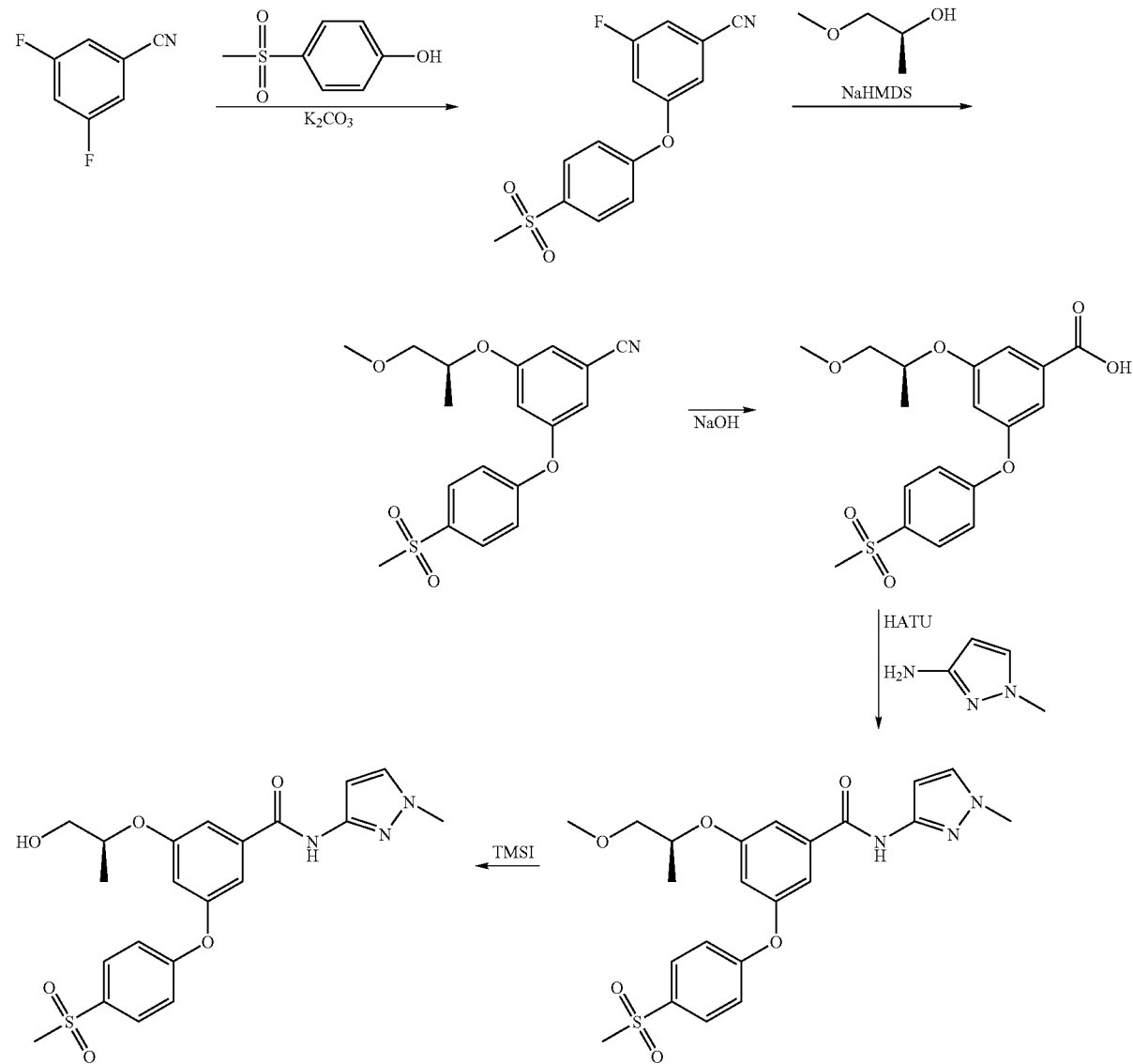

29
3-Fluoro-5-[4-(methanesulfonyl)phenoxy]benzonitrile

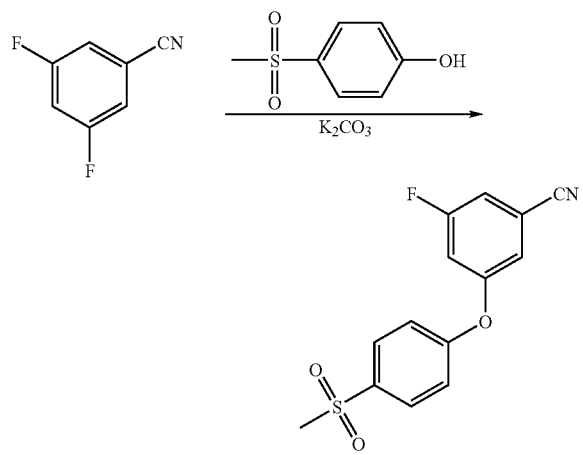

4-Methanesulfonyl-phenol (7.6 g, 44 mmol) was stirred in dry DMF (61 ml), anhydrous potassium carbonate (9.1 g, 66 mmol) was added and the mixture was heated to 13° C. for 1 hour. 3,5-Difluoro-benzonitrile (6.1 g, 44 mmol) was added and the mixture was stirred and heated to 130° C. for 18 hours. The reaction mixture was cooled to room temperature, water (183 ml) was added, and the resulting precipitate was isolated by filtration (3.0 g). The aqueous DMF was extracted with toluene (3×122 ml), the toluene extract was washed with water (4×122 ml) and the solvent was removed in vacuo, to give 5.0 g of solid material. This was combined with the precipitate isolated earlier and purified by flash column chromatography (eluent 60% n-hexane 40% ethyl acetate) to give the title product (7.1 g, 56% yield) as a white solid.

$^1$H NMR (400 MHz, CDCl$_3$) δ: 3.09 (s, 3H), 7.04 (d, 1H), 7.13 (s, 1H), 7.20 (m, 3H), 8.00 (d, 2H)

Alternative Method:

3,5-Difluorobenzonitrile (23.23 mmol; 3.23 g) was added to a 100 ml round bottomed flask followed by anhydrous potassium carbonate (17.42 mmol, 2.43 g), and then extra dry NMP (15.5 ml) and extra dry DMF (2 ml). The temperature was raised to 130° C. and the solution stirred until the reaction mixture became dark brown in colour. 4-Methanesulfonyl phenol (11.61 mmol; 2.0 g) dissolved in NMP (2.5 ml) was then added by syringe pump over 1 hr and the mixture was stirred at 130° C. for 3 hrs. The reaction mixture was cooled to 60° C. and toluene (20 ml) was added, followed by water (20 ml). The two layers were separated and the aqueous/NMP/DMF layer was re-extracted with toluene (20 ml). The combined toluene extracts were washed with water (3×20 ml). The organic layer was then cooled from 60° C. to 20° C. over 4 hrs, the precipitate was removed by filtration, the toluene filtrate was distilled down to low volume (~10 ml) and the residual white slurry was warmed 50° C. iso-Hexane (40 ml) was added and the temperature was reduced to 20° C. over 4 hrs. The product was isolated by filtration (2.81 g; 82.7%).

30
3-(4-Methanesulfonyl-phenoxy)-5-(2-methoxy-1-methyl-ethoxy)benzonitrile

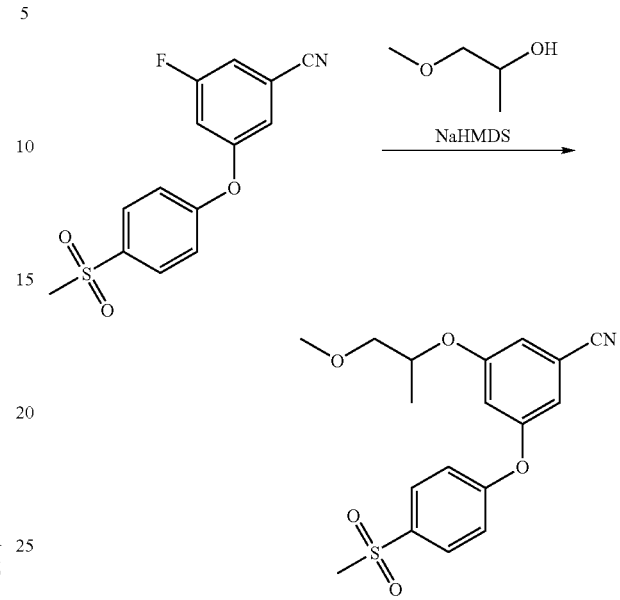

NaHMDS (0.63 g, 3.4 mmol) was placed in a 50 ml round bottomed flask (purged with nitrogen), dry DMF (5 ml) was added and the mixture was cooled to 0-5° C. 1-Methoxypropan-2-ol (0.31 g, 3.4 mmol) was added (exothermic), the mixture was slowly warmed to room temperature and stirred at this temperature for 30 minutes. 3-Fluoro-5-(4-methanesulfonyl-phenoxy)benzonitrile (1.0 g, 3.4 mmol) was dissolved in dry DMF (5 ml) and added to the reaction mixture, which was then stirred and heated to 70° C. for 18 hours. The reaction mixture was cooled to room temperature, water was added (30 ml) then the mixture was extracted with toluene (3×30 ml). The combined toluene extracts were washed with water (4×30 ml) and the solvent was evaporated in vacuo to give 1.0 g of clear oil, which was purified by flash column chromatography (eluent 60% n-hexane 40% ethyl acetate) to give the title product as a clear oil (0.74 g, 60% yield).

$^1$HNMR (400 MHz, CDCl$_3$) δ: 7.95 (d, 2H), 7.14 (d, 2H), 7.04 (m, 1H), 6.90 (m, 1H), 6.87 (m, 1H), 4.54 (m, 1H), 3.53 (m, 2H), 3.39 (s, 3H), 3.08 (s, 3H), 1.32 (d, 3H).

3-[(1S)-2-methoxy-1-methylethoxy]-5-[4-(methylsulfonyl)phenoxy]benzonitrile

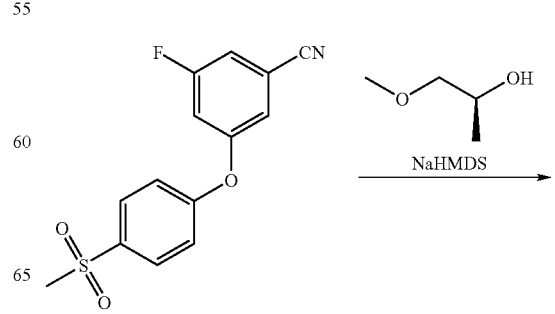

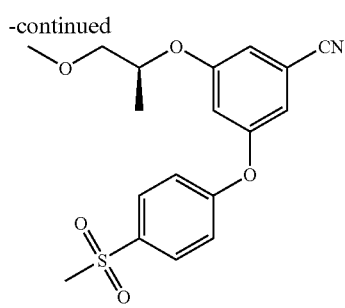

NaHMDS (24.5 mmol; 4.74 g) was charged to a 50 ml round bottomed flask, followed by dry DMF (32.5 ml). The flask was purged with nitrogen, the mixture was cooled to 0-5° C. and S-1-methoxypropan-2-ol (22.31 mmol; 2.01 g) was added over 5 minutes keeping the temperature below 6° C. The mixture was held at 0-5° C. for 25 minutes and then slowly warmed to room temperature over 35 minutes.

3-Fluoro-5-(4-methanesulfonyl-phenoxy)-benzonitrile (22.31 mmol; 6.50 g) was dissolved in dry DMF (32.5 ml) and this was added to the flask containing the anion of S-1-methoxyproapan-2-ol. The mixture was heated to 70° C. and held at 70° C. for 18 hrs. Water (20 ml) was added, then sufficient toluene to dissolve the precipitated solid was added. The mixture was extracted further with toluene (3×100 ml) and the combined toluene extract was washed with water (3×200 ml). The toluene layers were distilled down to low volume in vacuo and iso-hexane was added (50 ml). The resulting precipitate of the desired product was filtered off, washed with iso-hexane (2×25 ml) and dried in a vacuum oven at 40° C. overnight (6.0 g, 74.4% yield).

$^1$HNMR (400 MHz, CDCl$_3$) δ: 7.95 (d, 2H), 7.14 (d, 2H), 7.04 (m, 1H), 6.90 (m, 1H), 6.87 (m, 1H), 4.54 (m, 1H), 3.53 (m, 2H), 3.39 (s, 3H), 3.08 (s, 3H), 1.32 (d, 3H).

3-(4-Methanesulfonyl-phenoxy)-5-(2-methoxy-1-methyl-ethoxy)benzoic acid

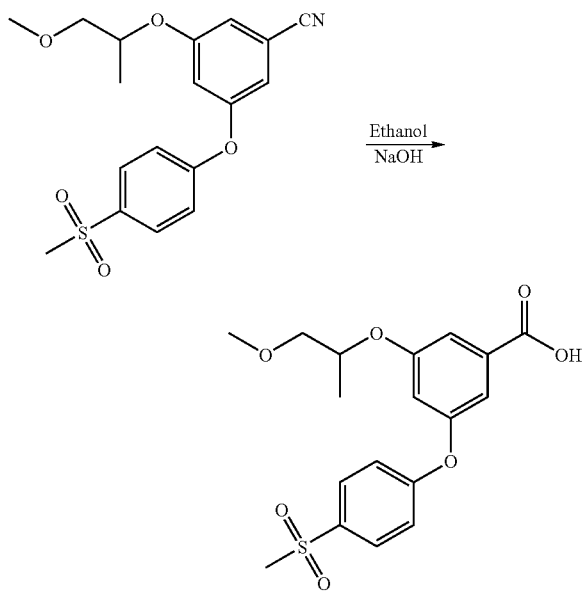

3-(4-Methanesulfonyl-phenoxy)-5-(2-methoxy-1-methyl-ethoxy)benzonitrile (0.1 g, 0.27 mmol) was dissolved in ethanol (1.0 ml) and charged to a 5 ml round bottomed flask equipped with a condenser. Water (0.2 ml, 11.1 mmol) was added, followed by sodium hydroxide (18.9M in water, 0.2 ml, 3.78 mmol). The reaction mixture was heated to reflux for 18 hours. The reaction mixture was cooled to room temperature, the solvent was evaporated in vacuo, the residue was partitioned between water (10 ml) and MTBE (10 ml) and the layers were separated. The aqueous phase was acidified to pH 1 with 2M HCl (2.5 ml, 5 mmol) and MTBE (10 ml) was added to extract the product. This MTBE extract was dried over MgSO$_4$, and then evaporated in vacuo to give the title product as a white solid (0.1 g, 100% yield).

$^1$H NMR (400 MHz, CDCl$_3$) δ: 7.92 (d, 2H), 7.51 (m, 1H), 7.35 (m, 1H), 7.12 (d, 2H), 6.90 (m, 1H), 4.63 (m, 1H), 3.57 (m, 2H), 3.42 (s, 3H), 3.08 (s, 3H), 1.33 (d, 3H).

3-[(1S)-2-Methoxy-1-methylethoxy]-5-[4-(methylsulfonyl)phenoxy]benzoic acid

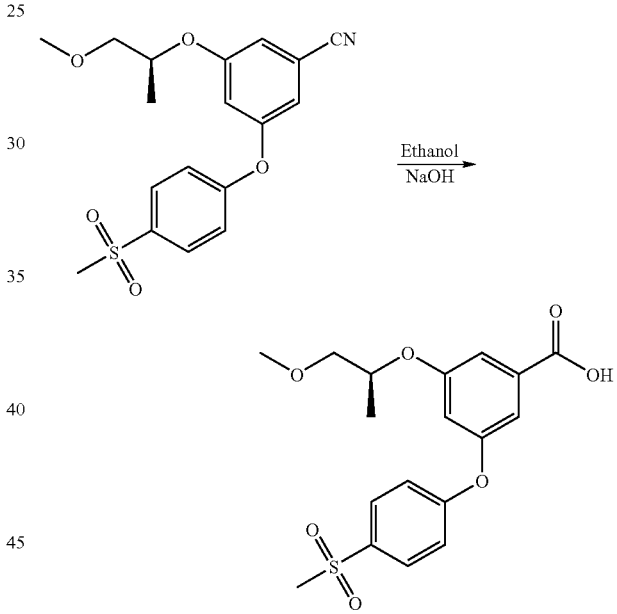

3-[(1S)-2-Methoxy-1-methylethoxy]-5-[4-(methylsulfonyl)phenoxy]benzonitrile (0.1 g, 0.27 mmol) was dissolved in ethanol (1.0 ml) and charged to a 5 ml round bottomed flask equipped with condenser and magnetic stirrer. Water (0.2 ml, 11.1 mmol) was added, followed by sodium hydroxide (18.9M in water, 0.2 ml, 3.78 mmol). The reaction mixture was heated to reflux for 18 hours. The reaction mixture was cooled to ambient temperature, and the solvent was evaporated in vacuo. The residue was partitioned between water (10 ml) and MTBE (10 ml) and the layers were separated. The aqueous phase was acidified to pH1 with 2M HCl (2.5 ml, 5 mmol) and MTBE (10 ml) was added to extract the product. The MTBE extract was dried over MgSO$_4$, and then evaporated in vacuo to afford a pale yellow oil (0.1 g, 100% yield).

$^1$H NMR (400 MHz, CDCl$_3$) δ: 7.92 (d, 2H), 7.51 (m, 1H), 7.35 (m, 1H), 7.12 (d, 2H), 6.90 (m, 1H), 4.63 (m, 1H), 3.57 (m, 2H), 3.42 (s, 3H), 3.08 (s, 3H), 1.33 (d, 3H).

3-[1(1S)-2-Methoxy-1-methylethoxy]-N-(1-methyl-1H-pyrazol-3-yl)-5-[4-(methylsulfonyl)phenoxy] benzamide

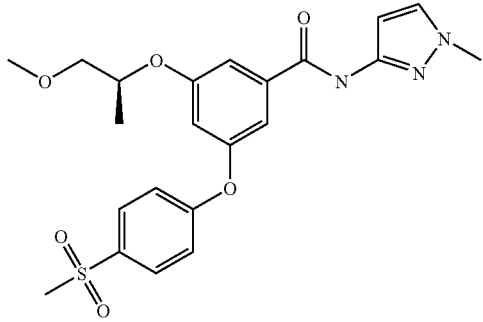

Diisopropylethylamine (2.5 equivalents) was added to a suspension of 3-{(1S)-2-methoxy-(1-methylethyl)oxy}-5-{[4-(methylsulfonyl)phenyl]oxy}benzoic acid (2.0 g, 5.25 mmol), O-(7-azabenzotriazol-1-yl)-N,N,N',N'-tetramethyluronium hexafluorophosphate (HATU, 2.5 g, 6.6 mmol) and 1-methyl-1H-pyrazol-3-amine (0.64 g, 6.6 mmol) in DMF (20 ml). The initial suspension dissolved into a dark orange solution. The resulting mixture was stirred at ambient temperature for 2 hours. The DMF was removed in vacuo, and the residue azeotroped with toluene. Water was added and the mixture extracted with ethyl acetate. The extracts were combined and washed sequentially with 1M hydrochloric acid, saturated sodium hydrogen carbonate solution and brine. The solution was dried (MgSO$_4$), filtered, and evaporated in vacuo to give the crude product which was chromatographed (50% ethyl acetate in isohexane) to give desired compound (25% yield), and recovered starting material.

$^1$H NMR (300 MHz, d$_6$-DMSO) δ: 1.2 (d, 3H), 3.2 (s, 3H), 3.25 (s, 3H), 3.5 (m, 2H), 3.8 (s, 3H), 4.75 (m, 1H), 6.55 (s, 1H), 6.9 (s, 1H), 7.2 (d, 2H), 7.3 (s, 1H), 7.45 (s, 1H), 7.6 (s, 1H), 7.9 (d, 2H), 10.85 (br s, 1H) m/z: 460 (M+H)$^+$.

3-[(1S)-2-Hydroxy-1-methylethoxy]-N-(1-methyl-1H-pyrazol-3-yl)-5-[4-(methylsulfonyl)phenoxy] benzamide

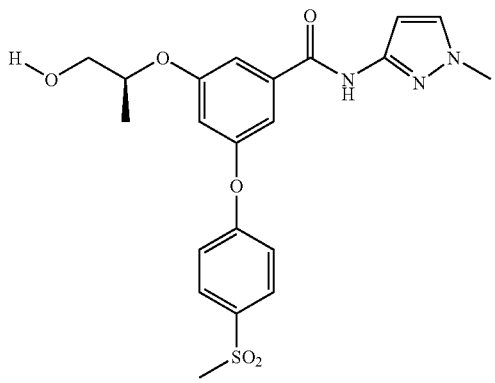

Trimethylsilyl iodide (11.06 ml, 76.25 mmol) was added to a solution of 3-[(1S)-2-methoxy-1-methylethoxy]-N-(1-methyl-1H-pyrazol-3-yl)-5-[4-(methylsulfonyl)phenoxy]benzamide (7.00 g, 15.25 mmol) in dry acetonitrile (100 ml) under argon for 21 h. Water (40 ml) was added to quench the reaction and the acetonitrile was removed in vacuo. The residue was diluted with ethyl acetate (200 ml) and 1M aqueous hydrochloric acid and the organic layer was separated and further washed with 10% w/v aqueous sodium thiosulfate pentahydrate to remove residual iodine. The organic layer was separated, dried (MgSO$_4$), filtered and evaporated and purified by column chromatography (eluting with 3% to 5% methanol: dichloromethane) to give the title compound (5.70 g, 84%) as a white foam. Recrystallisation from hot ethanol (125 mg/ml) afforded the title compound as colourless needles (87% recovery); $^1$H NMR (300 MHz, CDCl$_3$) δ: 1.33 (d, 3H), 2.10 (t, 1H), 3.08 (s, 3H), 3.78 (m, 2H), 3.82 (s, 3H), 4.57 (m, 1H), 6.80 (m, 2H), 7.15 (m, 3H), 7.25 (m, 2H), 7.93 (d, 2H), 8.43 (s, 1H); m/z 444 (M−H)$^−$.

EXAMPLE 2

This example illustrates formation of a compound of formula (VIII).

3-(3,5-Difluorophenoxy)-5-(2-methoxy-1-methylethoxy)benzoic acid

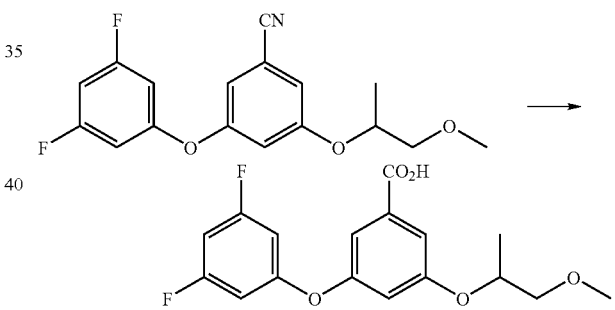

3-(3,5-difluorophenoxy)-5-(2-methoxy-1-methylethoxy)benzonitrile (1.00 equiv; 9.40 mmol; 3.00 g) was charged to a 100 ml round-bottomed flask (1 neck, condenser, magnetically stirred) with ethanol (515 mmol; 30.0 ml; 23.7 g). Water (138 mmol; 2.49 ml; 2.49 g), then sodium hydroxide (18.9M in water, 47.0 mmol; 2.49 ml; 3.75 g) was charged and the mixture heated to reflux (bath temperature 90° C.) for 4 hours. The mixture was cooled and solvent removed in vacuo affording a colourless solution (water not removed). The mixture was partitioned between water (50 ml) and MTBE (50 ml) and the layers separated (aqueous layer pH=14). The aqueous phase was acidified with HCl solution (2M, aq, 50 ml) and extracted with MTBE (50 ml). The organic layer was dried over MgSO$_4$, filtered and the volatiles removed in vacuo affording 3-(3,5-difluorophenoxy)-5-(2-methoxy-1-methylethoxy)benzoic acid as a colourless oil (3.15 g, 99%).

$^1$H NMR (400 MHz, CDCl$_3$) δ: 7.49 (m, 1H), 7.34 (m, 1H), 6.87 (m, 1H), 6.54 (m, 3H), 4.62 (m, 1H), 3.57 (m, 2H), 3.42 (s, 3H), 1.34 (d, 3H).

3-(3,5-Difluorophenoxy)-5-(2-methoxy-1-methylethoxy)benzonitrile

3-Bromo-5-(2-methoxy-1-methylethoxy)benzonitrile

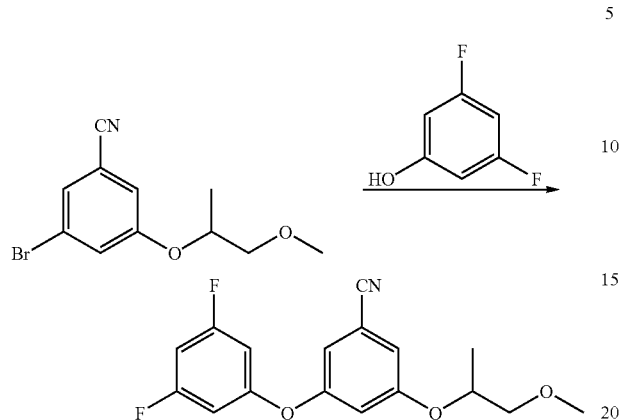

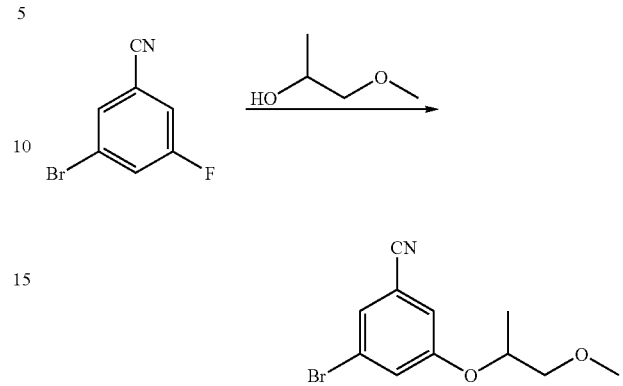

3,5-Difluorophenol (2.00 equiv; 51.8 mmol; 6.74 g) was charged to a 100 ml round-bottomed flask (3 necks, 2 stoppers, air condenser with argon inlet, magnetically stirred, oven dried) followed by NMP (471 mmol; 45.3 ml; 46.7 g) and cesium carbonate (51.8 mmol; 16.9 g). The mixture was sparged with argon for 10 minutes then cuprous monochloride (6.48 mmol; 641 mg), 2,2,6,6-tetramethyl-3,5-heptanedione, (1.30 mmol; 271 µl; 239 mg) and 3-bromo-5-(2-methoxy-1-methylethoxy)benzonitrile (1.00 equiv; 25.9 mmol; 7.00 g) were charged sequentially. The mixture was sparged with argon for 5 minutes then heated to 120° C. and stirred for 24 hours. The reaction mixture was cooled and partitioned between HCl solution (1M, aqueous, 200 ml) and MTBE (200 ml). The layers were separated and the organic portion washed with NaOH solution (1M, aq, 200 ml), water (200 ml) and brine (200 ml). The resultant organic solution was dried over MgSO$_4$, filtered and the solvent removed in vacuo affording a brown oil. This material was purified by flash column chromatography affording 3-(3,5-difluorophenoxy)-5-(2-methoxy-1-methylethoxy)benzonitrile as a pale yellow oil (5.17 g, 63%). $^1$H NMR (400 MHz, CDCl$_3$) δ: 7.01 (s, 1H), 6.86 (m, 2H), 6.62 (m, 1H), 6.53 (m, 2H), 4.54 (m, 1H), 3.53 (m, 2H), 3.39 (s, 3H), 1.32 (d, 3H).

NaHMDS (148 mmol; 27.2 g) was charged to a 1000 ml round-bottomed flask (4 necks, thermometer, pressure-equalising dropping funnel, stopper, nitrogen inlet, magnetically stirred, oven dried, nitrogen purged), followed by DMF (300 ml). The mixture was stirred for 5 minutes then 1-methoxy-2-propanol (1.50 equiv; 148 mmol; 14.3 ml; 13.4 g) was added dropwise over a 10-minute period. The reaction temperature increased to 25° C. The mixture was cooled using a cold-water bath to 23° C., then 3-bromo-5-fluorobenzonitrile (1.00 equiv; 99.0 mmol; 20.0 g) in DMF (90 ml) was added over a 5 minutes period (cold water bath still present). The mixture warmed to 27° C. during addition, turning from yellow to brown. A line wash of DMF (10 ml) was added. The mixture was stirred at ambient temperature for 30 minutes, then quenched by addition of HCl solution (2M, aqueous, 200 ml), the dark brown reaction mixture turning pale yellow. The mixture was poured into water (400 ml) and extracted with EtOAc (3×400 ml). The combined organic extracts were washed with water (3×400 ml) and dried over MgSO$_4$, filtered and the solvent removed in vacuo affording 3-bromo-5-(2-methoxy-1-methylethoxy)benzonitrile as an orange oil (25.38 g, 95%). $^1$H NMR (400 MHz, CDCl$_3$) δ: 7.32 (s, 1H), 7.26 (s, 1H), 7.11 (s, 1H), 4.58-4.55 (m, 1H), 3.59-3.48 (m, 2H), 3.41 (s, 3H), 1.33-1.31 (d, 3H).

EXAMPLE 3

Synthetic Route

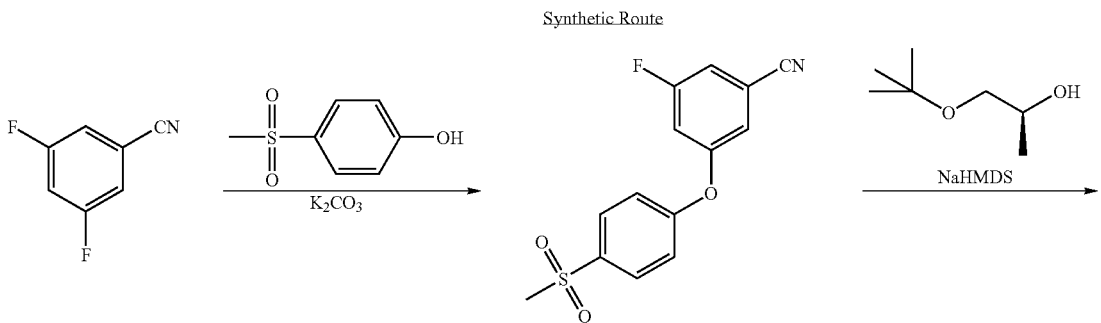

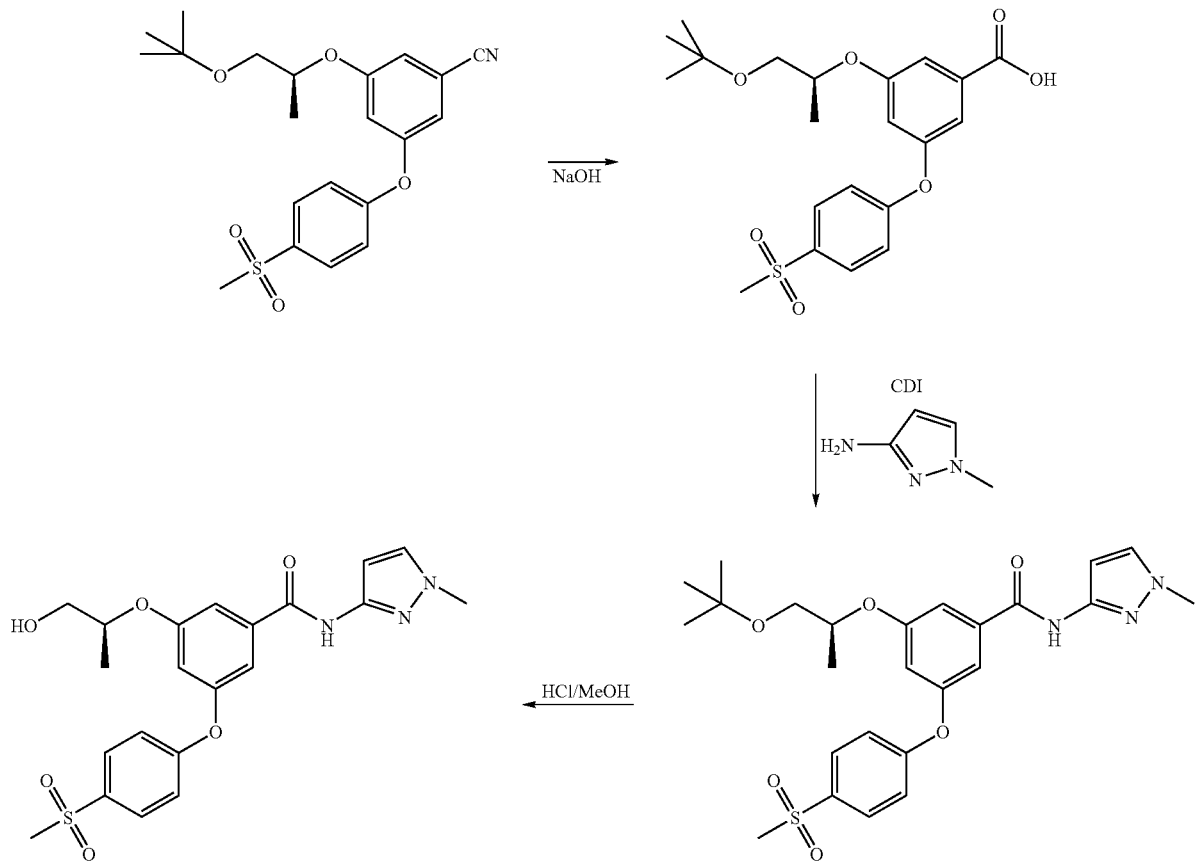

3-[(1S)-2-tert-Butoxy-1-methylethoxy]-5-[4-(methylsulfonyl)phenoxy]benzonitrile

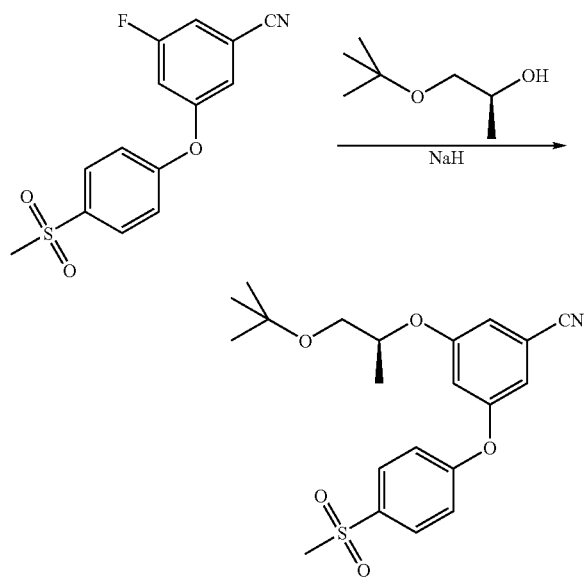

To a 3-necked round-bottomed flask (100 ml with condenser, septum thermometer and magnetic follower) was charged sodium hydride (32.96 mmol, 1.32 g). The flask was placed under an inert atmosphere and dry NMP (80 ml) was charged. To the resulting suspension was charged (S)-1-tert-butoxy-2-propanol (30.21 mmol; 3.99 g; added in 0.2 ml aliquots with temperature control to control $H_2$ evolution). Once gas evolution had ceased 3-fluoro-5-(4-methanesulfonyl-phenoxy)benzonitrile (see Example 1, 27.46 mmol, 8.0 g) was added in one portion. The reaction mixture was heated to 70° C. for 3 hours. The reaction was cooled to room temperature and toluene (240 ml) was added followed by water (240 ml). The contents were stirred at room temperature for 30 minutes and then transferred to a separating funnel. The two layers were separated and the aqueous layer was further extracted with toluene (240 ml). The organic extracts were combined and washed once with sodium hydroxide (160 mmol, 160 ml) and then with water (4×160 ml). The toluene was removed in vacuo to leave an oil that slowly solidified (9.20 g; 83.02% yield).

$^1$H NMR (400 MHz, d-6 DMSO) δ: 7.92 (d, 2H) 7.33 (s, 1H); 7.23 (d, 2H); 7.19 (s, 1H); 7.07 (t, 1H); 4.62 (m, 1H); 3.44 (m, 2H); 3.19 (s, 3H); 1.21 (d, 3H); 1.07 (s, 9H).

3-[(1S)-2-tert-Butoxy-1-methylethoxy]-5-[4-(methylsulfonyl)phenoxy]benzoic acid

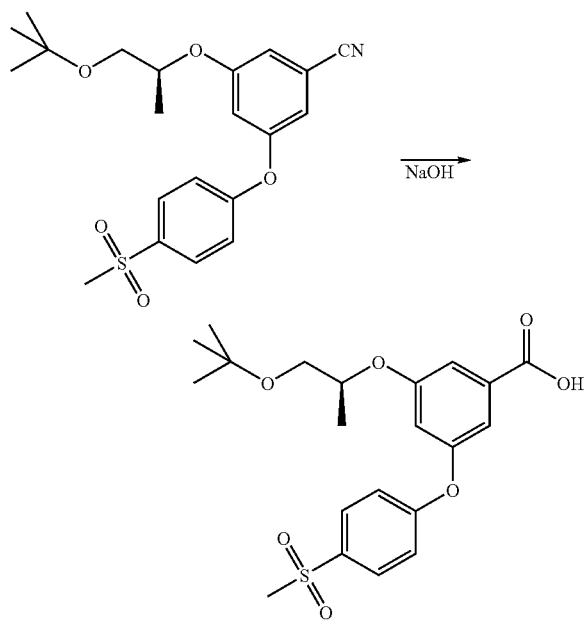

3-[(1S)-2-tert-Butoxy-1-methylethoxy]-5-[4-(methylsulfonyl)phenoxy]benzonitrile (23.7 mmol; 9.56 g) was dissolved in ethanol (95.60 ml), and transferred to a 250 ml round bottomed flask, using ethanol (5 ml) to wash the residual solid from the flask. Water (6.25 ml) and sodium hydroxide (118.5 mmol; 6.30 ml) was added and the reaction was heated to reflux for 18 hours. The ethanol was removed in vacuo. The residual yellow suspension was dissolved in MTBE (162.5 ml) and water (162.5 ml). The two layers were separated, the MTBE layer was discarded and the aqueous layer was acidified with 2M HCl (100 ml). The aqueous layer was extracted twice with MTBE (162.5 ml). The organic extracts were combined and dried with magnesium sulfate, the MTBE was removed in vacuo, to give the desired product (7.0 g, 69.9% yield).

$^1$H NMR (400 MHz, d-6 DMSO) δ: 7.92 (d, 2H), 7.32 (s, 1H), 7.21 (d, 2H), 7.10 (s, 1H), 7.00 (t, 1H), 4.53 (m, 1H), 3.42 (m, 2H), 3.19 (s, 3H), 1.22 (d, 3H), 1.09 (s, 9H).

({3-[(1S)-2-tert-Butoxy-1-methylethoxy]-5-[4-(methylsulfonyl)phenoxy]benzoyl}oxy)(tert-butyl)ammonium

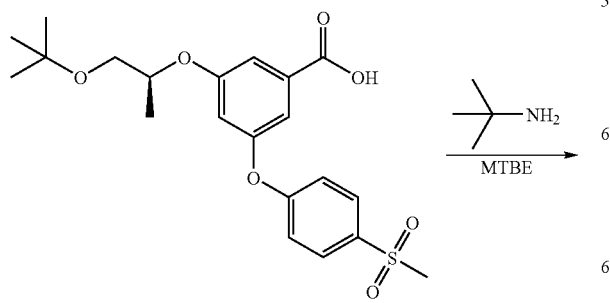

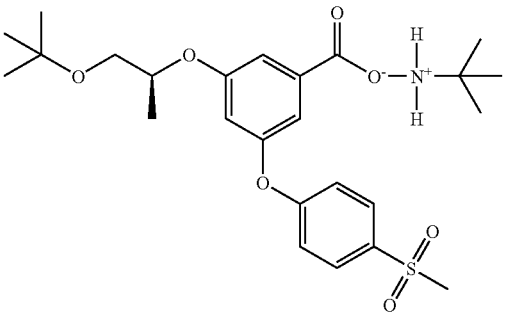

A solution of tert-butylamine was prepared by charging tert-butylamine (0.31 L, 2.94 mol) to a reaction vessel containing MTBE (2.27 L). The solution was stirred at ambient temperature and then charged into a second reaction vessel containing 3-[(1S)-2-tert-butoxy-1-methylethoxy]-5-[4-(methylsulfonyl)phenoxy]benzoic acid (1.13 Kg, 267 mol) and MTBE (2.54 L). The temperature was maintained between 20-30° C. during the addition, the residual tert-butylamine was washed in with MTBE (0.57 L). The reaction mixture was heated to 38-40° C. for 3 hours under a nitrogen atmosphere. The reaction mixture was cooled to 18-25° C. over 1-2 hours and then held until crystallisation occurred. The product was isolated by filtration washed twice with MTBE (2.28 L), and dried in a vacuum oven at 38-40° C. This resulted in (1.32 Kg, 100% yield) of the title compound.

$^1$H NMR (400 MHz, CDCl$_3$) δ 7.86 (d, 2H), 7.47 (s, 1H), 7.26 (s, 1H), 7.08 (d, 2H), 6.74 (t, 1H), 4.45 (sextet, 1H), 3.56 (dd, 1H), 3.37 (dd, 1H), 3.04 (s, 3H), 1.30 (d, 3H), 1.25 (s, 9H), 1.16 (s, 9H).

3-[(1S)-2-tert-Butoxy-1-methylethoxy]-5-[4-(methylsulfonyl)Phenoxy]benzoic acid

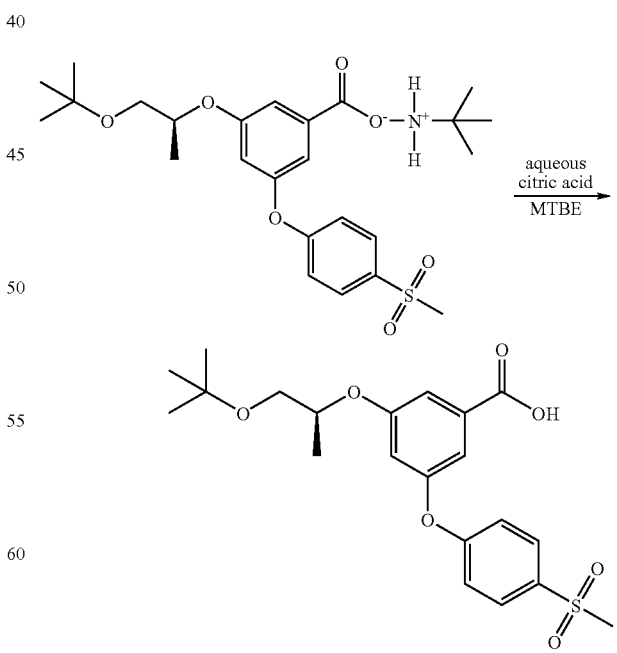

Aqueous citric acid was prepared by dissolving citric acid (7.35 g, 38.25 mmol) in water (100 mL). The aqueous citric acid solution was added to a reaction vessel containing ({3-[(1S)-2-tert-butoxy-1-methylethoxy]-5-[4-(methylsulfonyl)phenoxy]benzoyl}oxy)(tert-butyl)ammonium (10 g at 94.6% w/w, 19.13 mmol) and MTBE (80 mL). The two-phase mixture was stirred for 30 minutes at ambient temperature. The two phases were separated, and the aqueous phase was extracted with MTBE (80 mL). The two organic phases were combined and washed three times with brine (3×80 mL), followed by water (2×80 mL). The combined MTBE extract was distilled down to low volume, fresh MTBE (80 mL) was added and the mixture was distilled down to low volume. Acetonitrile (120 mL) was added and the mixture was distilled down to low volume at 50° C., 209 mbar. This azeodrying was repeated once more to provide a dry acetonitrile solution of the title compound, which was used directly in the next stage.

$^1$H NMR (400 MHz, CDCl$_3$) δ 7.91 (d, 2H), 7.54 (s, 1H), 7.33 (s, 1H), 7.12 (d, 2H), 6.91 (t, 1H), 4.53 (sextet, 1H), 3.58 (dd, 1H), 3.43 (dd, 1H), 3.07 (s, 3H), 1.34 (d, 3H), 1.19 (s, 9H).

3-[(1S)-2-tert-Butoxy-1-methylethoxy]-N-(1-methyl-1H-pyrazol-3-yl)-5-[4-(methylsulfonyl)phenoxy]benzamide

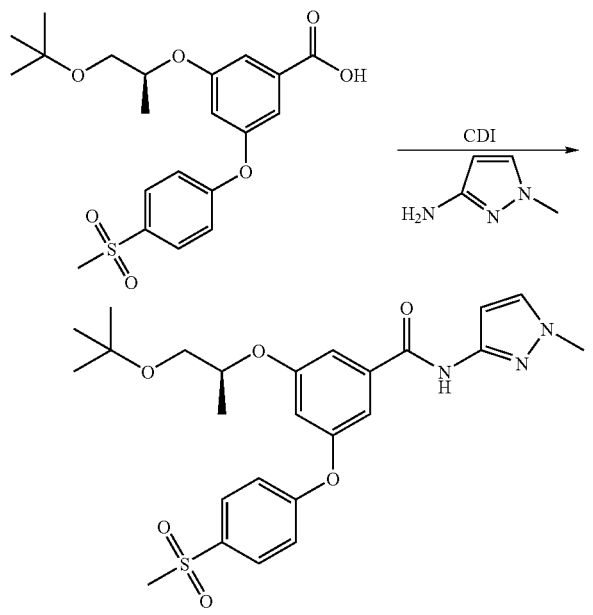

1,1'-Carbonyldiimidazole (CDI) (7.44 mmol, 1.21 g) was charged to a 25 ml 3-necked round bottomed flask (equipped with condenser, nitrogen line, magnetic stirrer, thermometer, and septum). The flask was placed under an inert atmosphere and THF (160.9 mmol, 13.1 ml) was added. 3-[(1S)-2-tert-Butoxy-1-methylethoxy]-5-[4-(methylsulfonyl)phenoxy]benzoic acid (6.20 mmol, 2.62 g) was dissolved in THF (10.48 ml) and added to the flask in 2 ml aliquots over 5 minutes, then washed in using further THF (5 ml). The solution was stirred at room temperature for 1 hour. The reaction temperature was increased to 60° C. and 3-amino 1-methylpyrazole (6.82 mmol; 662.2 ml) dissolved in toluene (13.1 ml) was added to the reaction in one portion then washed in using further toluene (4 ml). The reaction was held at 60° C. for 18 hours. The solvent was removed in vacuo to leave a thick yellow oil, MTBE (100 ml) and sodium hydroxide (1M, 50 ml) were added, the two layers were separated and the organic layer was washed with sodium hydroxide (1M, 20 ml) followed by HCl (2M, 30 ml). The organic layer was dried with magnesium sulfate and the solvent was removed in vacuo to give a thick yellow oil. A small quantity was purified using flash column chromatography (eluent 80% isopropyl acetate: 20% iso-hexane) to give the desired product.

$^1$H NMR (400 MHz, d-6 DMSO) δ: 10.89 (s, 1H), 7.96-7.92 (m, 2H), 7.60 (d, 1H), 7.50 (s, 1H), 7.29 (s, 1H), 7.27-7.21 (m, 2H,), 6.91 (t, 1H), 6.56 (d, 1H), 4.64-4.54 (m, 1H), 3.78 (s, 3H), 3.60-3.46 (m, 2H), 3.21 (s, 3H), 1.24 (d, 3H).

An Alternative Procedure:

To a dry 1 L-jacketed vessel under nitrogen atmosphere was charged acetonitrile (250 mL). Overhead stirring was commenced and the reaction warmed to 25° C. Once the reaction reached the required temperature CDI (149.11 mmol, 24.18 g) was charged to the reactor. A 39.8% w/w solution of 3-[(1S)-2-tert-butoxy-1-methylethoxy]-5-[4-(methylsulfonyl)phenoxy]benzoic acid in acetonitrile was then charged to the reaction as a constant flow over 90 minutes. Completion of this addition was followed by addition of a line wash of acetonitrile (50 mL). The resulting solution was then stirred at 25° C. for 30 minutes.

The reaction temperature was then increased to 60° C. and 3-amino 1-methylpyrazole (117.51 mmol, 17.24 g) dissolved in acetonitrile (50 mL) was charged to the reaction in one portion followed by an acetonitrile (50 mL) line wash. The reaction was held at 60° C. for 18 hours. HPLC analysis found the solution to contain 11.71% w/w of the required amide product. This represented a 91% yield (53.78 g; 100.72 mmol) of the title compound. The solution was used directly in the following reaction without isolation of the product.

$^1$H NMR (400 MHz, DMSO) 10.89 (s, 1H, NH), 7.96-7.92 (m, 2H), 7.60 (d, 1H), 7.50 (m, 1H), 7.30 (m, 1H), 7.26-7.22 (m, 2H), 6.91 (t, 1H), 6.56 (d, 1H), 4.70-4.62 (m, 1H), 3.78 (s, 3H), 3.60-3.46 (m, 2H), 3.21 (s, 3H), 1.25 (d, 3H).

3-[(1S)-2-Hydroxy-1-methylethoxy]-N-(1-methyl-1H-pyrazol-3-yl)-5-[4-(methylsulfonyl)phenoxy]benzamide

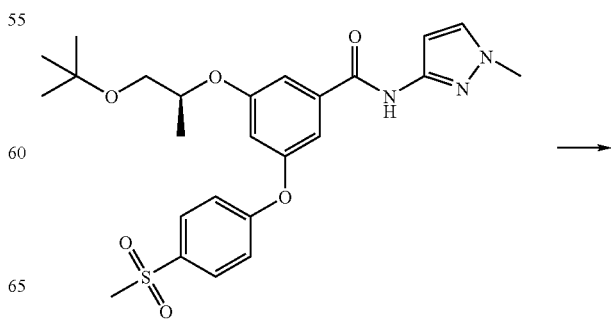

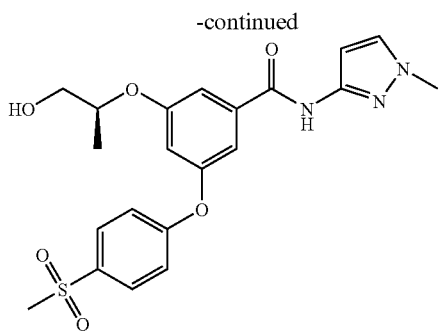

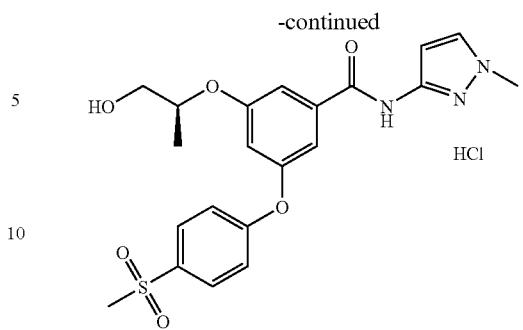

To a 25 ml round-bottomed flask was charged 3-[(1S)-2-tert-butoxy-1-methylethoxy]-N-(1-methyl-1H-pyrazol-3-yl)-5-[4-(methylsulfonyl)phenoxy]benzamide (498.4 μmol, 250.0 mg). This was dissolved in methanol (4 ml) and HCl (4 ml) was added to the flask in one portion. The reaction was heated to 50° C. for 1.5 hours. Solvent was removed in vacuo to yield a colourless solid that quickly changed to liquid form on standing. The liquid was dissolved in $^i$PrOAc (10 ml) and water (10 ml). The aqueous layer was extracted with further $^i$PrOAc (10 ml). The combined organic layer was dried with MgSO$_4$ and the solvent was removed in vacuo to yield crude title product (142 mg; 63.95% yield) as a white foamy solid.

A sample of this material (110 mg) was dissolved in ethanol (0.5 ml) and then heated to reflux. The solution was then cooled to room temperature and a small spatula of the product was added at 45-50° C. to provide a seed to aid recrystallisation. After several days stirring, the recrystallised solid was isolated by filtration to yield the desired product as a crystalline solid (50 mg, 45% yield).

$^1$H NMR (400 MHz, d-6 DMSO) δ: 10.89 (s, 1H), 7.97-7.92 (m, 2H), 7.60 (d, 1H), 7.50 (s, 1H), 7.30 (s, 1H), 7.27-7.22 (m, 2H), 6.91 (t, 1H), 6.57 (d, 1H), 4.88 (t, 1H), 4.63-4.55 (m, 1H), 3.77 (s, 3H), 3.60-3.52 (m, 1H), 3.21 (s, 3H), 1.24 (d, 3H).

An Alternative Procedure:

3-[(1S)-2-Hydroxy-1-methylethoxy]-N-(1-methyl-1H-pyrazol-3-yl)-5-[4-(methylsulfonyl)phenoxy]benzamide hydrochloride

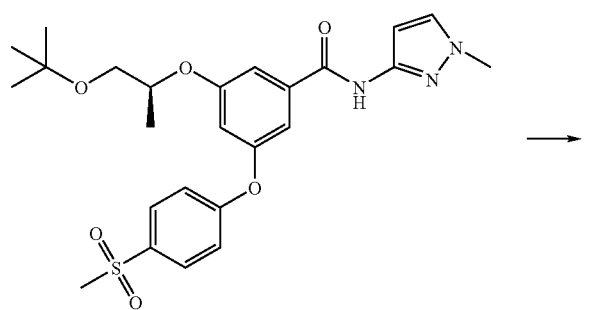

A solution of 3-[(1S)-2-tert-butoxy-1-methylethoxy]-N-(1-methyl-1H-pyrazol-3-yl)-5-[4-(methylsulfonyl)phenoxy]benzamide (456.32 g of an 11.41% w/w solution in acetonitrile; 103.80 mmol) was charged to a jacketed vessel. The stirred mixture was heated to between 93° C. and 101° C. (jacket temperature) and solvent was removed by distillation under atmospheric pressure until a total of 370 mL of distillate was collected. The mixture was then cooled (jacket temperature 30° C.) and MTBE (500 mL) was added to give a cloudy mixture. The jacket temperature was set to 20° C. and aqueous hydrochloric acid (250 mL of a 2.10M solution) was added when the temperature of the reaction mixture reached 23.6° C. The mixture was stirred for 10 minutes then separated. The upper organic layer washed with water (250 mL) and the layers were separated. The retained organic layer was heated (jacket temperature 68° C.) and solvent removed by distillation under atmospheric pressure until a total of 440 mL of distillate was collected. Isopropyl alcohol (300 mL) was then added to the mixture in the vessel. The jacket temperature was set to 95° C. and solvent removed by distillation under atmospheric pressure until a total of 250 mL of distillate was collected. The mixture was cooled to between 20 and 21° C. and a solution of hydrogen chloride (5.52 M in isopropanol, 616 mL) was added. The mixture was heated to 50° C. over 40 minutes. The mixture was maintained at 50° C. for a further 70 minutes before addition of a seed of 3-[(1S)-2-hydroxy-1-methylethoxy]-N-(1-methyl-1H-pyrazol-3-yl)-5-[4-(methylsulfonyl)phenoxy]benzamide (66 mg). The mixture was stirred for a further 15 min then seeded once more (53 mg). The mixture was set on a pre-programmed cooling ramp to 15° C. over 400 min. The product started to crystallise approximately 40 minutes after initiation of the cooling profile. After stirring for approximately 20 hours after initiation of the cooling ramp, the crystallised product was collected by filtration. The collected solid was washed with MTBE (150 mL). The product cake was sucked dry on the filter then subjected to further drying in vacuum for approximately 18 hours at 45° C. to give the title product (40.52 g; with a purity of 94.22% w/w by HPLC assay (73.4% yield after correction for assay)).

$^1$H NMR (400 MHz, DMSO) δ 10.90 (s, 1H), 7.97-7.91 (m, 2H), 7.60 (d, 1H), 7.50 (s, 1H), 7.30 (s, 1H), 7.27-7.22 (m, 2H), 6.91 (t, 1H), 6.56 (d, 1H), 5.52 (br s), 4.64-4.55 (m, 1H), 3.77 (s, 3H), 3.61-3.45 (m, 2H), 3.21 (s, 3H), 1.24 (d, 3H).

3-[(1S)-2-Hydroxy-1-methylethoxy]-N-(1-methyl-1H-pyrazol-3-yl)-5-[4-(methylsulfonyl)phenoxy]benzamide

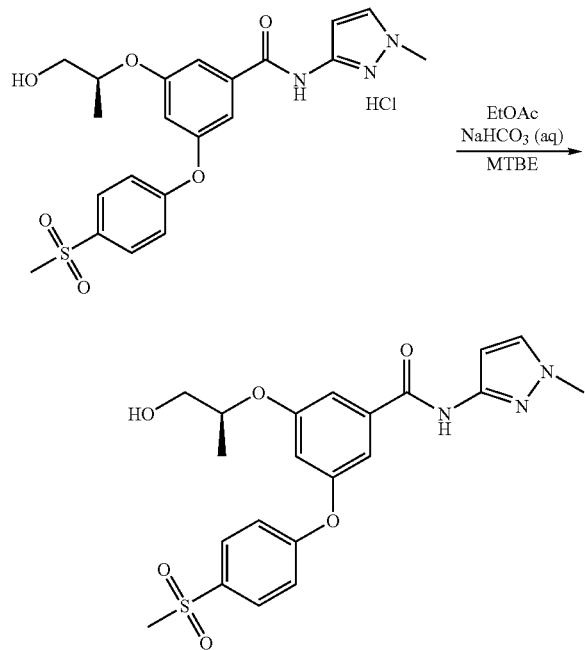

3-[(1S)-2-Hydroxy-1-methylethoxy]-N-(1-methyl-1H-pyrazol-3-yl)-5-[4-(methylsulfonyl)phenoxy]benzamide hydrochloride (2907.8 g, 6.03 mol) and ethyl acetate (30 L) were charged to the reaction vessel and stirred to give a thick cream slurry. Saturated aqueous sodium hydrogen carbonate solution (7.3 L) was charged to the reaction over at least 15 minutes (to control gas evolution). The mixture was stirred for at least 30 minutes until the solid had dissolved to give a clear solution. The aqueous phases was removed and discarded, the organic phase was washed with water (14.6 L), and screened into the crystallising vessel. The reaction mixture was azeo-dried by distillation; the ethyl acetate solution was distilled from 31.0 L down to 14.5 L, fresh ethyl acetate (14.5 L) was added and the distillation was repeated until there was 14.5 L of ethyl acetate remaining in the reaction vessel. The reaction mixture was cooled to 45° C. at −0.4° C./minute, and then held at 45° C. for 18 hours. The reaction mixture was seeded, MTBE (29 L) was added to the reaction mixture over ~1 hour, maintaining the reaction temperature at 45° C.; the mixture was then stirred at this temperature for 3 hours prior to cooling to 20° C. at −0.4° C./min. The mixture was held at 20° C. for 18 hours, the product was then isolated by filtration and washed with MTBE (6.0 L) and dried in a vacuum oven at 40° C. This resulted in 2216 g (82% yield) of the title product.

$^1$H NMR (400 MHz, DMSO) δ 10.86 (s, 1H), 7.91 (d, 2H), 7.56 (d, 1H), 7.47 (s, 1H), 7.26 (s, 1H), 7.20 (d, 2H), 6.88 (t, 1H), 6.53 (d, 1H), 4.85 (t, 1H), 4.55 (sextet, 1H), 3.73 (s, 3H), 3.57-3.42 (m, 2H), 3.17 (s, 3H), 1.20 (d, 3H).

$^{13}$C NMR (100 MHz, DMSO) δ 162.98, 160.80, 159.46, 155.85, 146.78, 136.76, 135.15, 130.89, 129.59, 118.19, 111.07, 110.91, 110.79, 97.41, 75.09, 64.08, 43.74, 38.29, 16.38

REFERENCES

1. Printz, R. L., Magnuson, M. A. and Granner, D. K. (1993) Annual Review of Nutrition 13, 463-96
2. DeFronzo, R. A. (1988) Diabetes 37, 667-87
3. Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4. Bell, G. I., Pilkis, S. J., Weber, I. T. and Polonsky, K. S. (1996) Annual Review of Physiology 58, 171-86
5. Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6. Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
6a. Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440
7. Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30
8. Caro, J. F., Triester, S., Patel, V. K., Tapscott, E. B., Frazier, N. L. and Dohm, G. L. (1995) Hormone & Metabolic Research 27, 19-22
9. Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10. Shiota, M., Postic, C., Fujimoto, Y., Jetton, T. L., Dixon, K., Pan, D., Grimsby, J., Grippo, J. F., Magnuson, M. A. and Chemington, A. D. (2001) Diabetes 50, 622-9
11. Ferre, T., Pujol, A., R$^{1a}$, E., Bosch, F. and Valera, A. (1996) Proceedings of the National Academy of Sciences of the United States of America 93, 7225-30
12. Seoane, J., Barbera, A., Telemaque-Potts, S., Newgard, C. B. and Guinovart, J. J. (1999) Journal of Biological Chemistry 274, 31833-8
13. Moore, M. C., Davis, S, N., Mann, S. L. and Chemington, A. D. (2001) Diabetes Care 24, 1882-7
14. Alvarez, E., Roncero, I., Chowen, J. A., Vazquez, P. and Blazquez, E. (2002) Journal of Neurochemistry 80, 45-53
15. Lynch, R. M., Tompkins, L. S., Brooks, H. L., Dunn-Meynell, A. A. and Levin, B. E. (2000) Diabetes 49, 693-700
16. Roncero, I., Alvarez, E., Vazquez, P. and Blazquez, E. (2000) Journal of Neurochemistry 74, 1848-57
17. Yang, X. J., Kow, L. M., Funabashi, T. and Mobbs, C. V. (1999) Diabetes 48, 1763-1772
18. Schuit, F. C., Huypens, P., Heimberg, H. and Pipeleers, D. G. (2001) Diabetes 50, 1-11
19. Levin, B. E. (2001) International Journal of Obesity 25, supplement 5, S68-S72.
20. Alvarez, E., Roncero, I., Chowen, J. A., Thorens, B. and Blazquez, E. (1996) Journal of Neurochemistry 66, 920-7
21. Mobbs, C. V., Kow, L. M. and Yang, X. J. (2001) American Journal of Physiology—Endocrinology & Metabolism 281, E649-54

22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dumi-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20
32 Jetton T. L., Liang Y., Pettepher C. C., Zimmerman E. C., Cox F. G., Horvath K., Matschinsky F. M., and Magnuson M. A., J. Biol. Chem., February 1994; 269: 3641-3654.
33 Reimann F. and Gribble F. M., Diabetes 2002 51: 2757-2763
34 Cheung A. T., Dayanandan B., Lewis J. T., Korbutt G. S., Rajotte R. V., Bryer-Ash M., Boylan M. O., Wolfe M. M., Kieffer T. J., Science, Vol 290, Issue 5498, 1959-1962, 8 Dec. 2000.

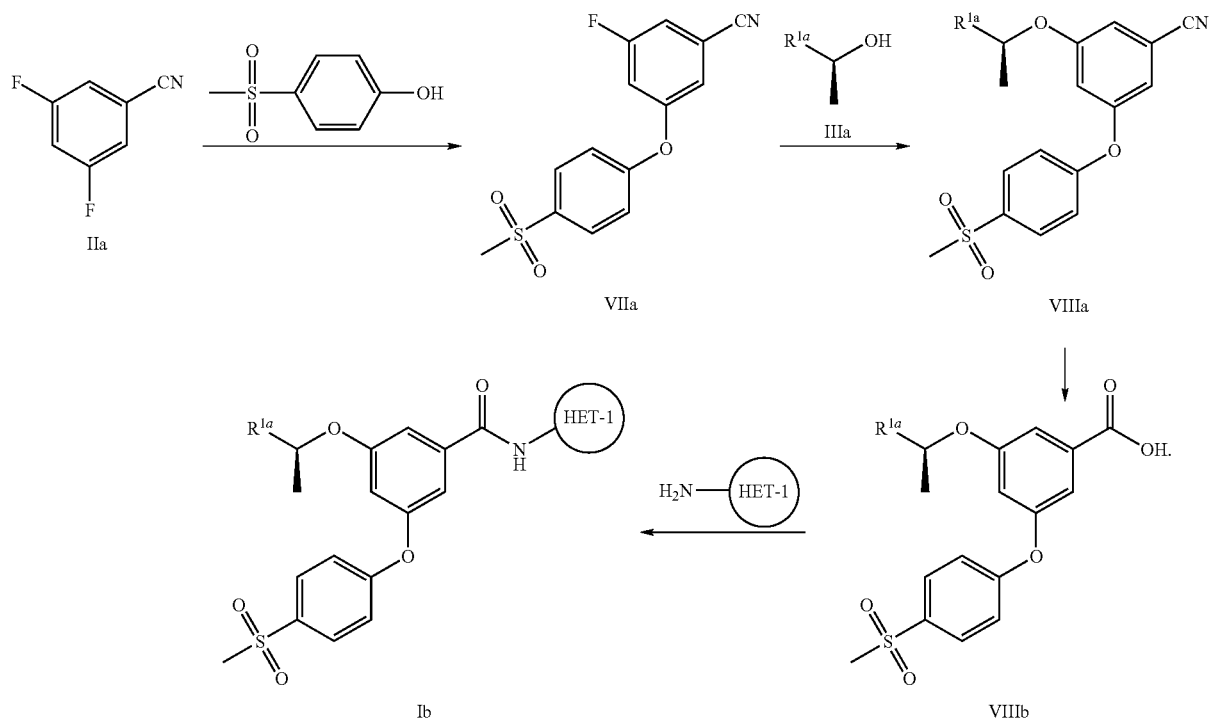

The invention claimed is:
1. A process for making a compound of formula (I),

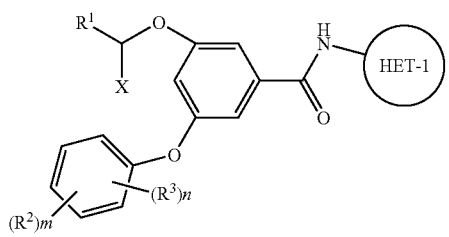

the process comprising
(a) reacting a compound of formula (II)

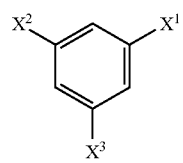

wherein $X^1$ is carboxyl or a precursor therefore, $X^2$ is F and $X^3$ is selected from F, Br and OH; with:
(i) a compound of formula (III) by nucleophilic aromatic substitution of $X^2$ using a suitable base in a suitable solvent,

wherein X is as defined for formula (I) below and $R^1$ is selected from methyl, methoxymethyl and hydroxymethyl or a protected version thereof; and
(ii) a compound of formula (IV) by nucleophilic aromatic substitution using a suitable base in a suitable solvent, or, when $X^3$ is Br, under conditions suitable for an Ullman ether reaction,

wherein $R^2$, $R^3$, m and n are as defined for formula (I) and $X^4$ is OH when $X^3$ is F or Br, and $X^4$ is a leaving group when $X^3$ is OH;
(b) optionally, converting $X^1$ into a carboxylic acid; and
(c) coupling of the carboxylic acid group to a compound of formula (V);

and thereafter optionally:
(i) converting a compound of formula (I) into another compound of formula (I);
(ii) where $R^1$ is a protected version of hydroxymethyl, removal of the protecting group;
(iii) forming a pro-drug; and/or
(iv) forming a pharmaceutically acceptable salt;
wherein in a compound of formula (I):
$R^1$ is hydroxymethyl, methoxymethyl or methyl;
X is methyl or ethyl;
$R^2$ is selected from —C(O)NR$^4$R$^5$, —SO$_2$NR$^4$R$^5$, —S(O)$_p$R$^4$ and HET-2;
HET-1 is a five or six membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;
HET-2 is a four, five or six membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to a S(O) or S(O)$_2$ group, which ring is optionally substituted on an available carbon or nitrogen atom by 1 or 2 substituents independently selected from $R^7$;

R³ is selected from halo, fluoromethyl, difluoromethyl, trifluoromethyl, $C_{1-3}$alkyl, $C_{1-3}$alkoxy and cyano;

R⁴ is selected from hydrogen; (1-4C)alkyl optionally substituted with 1 or 2 substituents independently selected from HET-2, —OR⁵, —SO₂R⁵, (3-6C)cycloalkyl (optionally substituted with 1 group selected from R⁷) and —C(O)NR⁵R⁵; (3-6C)cycloalkyl (optionally substituted with 1 group selected from R⁷); and HET-2;

R⁵ is hydrogen or (1-4C)alkyl;

or R⁴ and R⁵ together with the nitrogen atom to which they are attached may form a heterocyclyl ring system as defined by HET-3;

R⁶ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl and HET-4;

or, when HET-1 is 2-pyridyl, R⁶ may additionally be carboxy;

R⁷ is selected from —OR⁵, (1-4C)alkyl, —C(O)(1-4C)alkyl, —C(O)NR⁴R⁵, (1-4C)alkoxy(1-4C)alkyl, hydroxy(1-4C)alkyl and —S(O)$_p$R⁵;

HET-3 is an N-linked, four to six membered, saturated or partially unsaturated heterocyclyl ring, optionally containing 1 or 2 further heteroatoms independently selected from O, N and S, wherein a —CH₂— group can optionally be replaced by a —C(O)— and wherein a sulphur atom in the ring may optionally be oxidised to a S(O) or S(O)₂ group; which ring is optionally substituted on an available carbon or nitrogen atom by 1 or 2 substituents independently selected from R⁸; or HET-3 is an N-linked, seven membered, saturated or partially unsaturated heterocyclyl ring, optionally containing 1 further heteroatom independently selected from O, S and N, wherein a —CH²— group can optionally be replaced by a —C(O)— group and wherein a sulphur atom in the ring may optionally be oxidised to a S(O) or SO(O)₂ group; which ring is optionally substituted on an available carbon or nitrogen atom by 1 or 2 substituents independently selected from R⁸; or HET-3 is an N-linked 6-10 membered bicyclic saturated or partially unsaturated heterocyclyl ring, optionally containing 1 further nitrogen atom, wherein a —CH₂— group can optionally be replaced by a —C(O)—; which ring is optionally substituted on an available carbon or nitrogen atom by 1 substituent selected from hydroxy and R³;

R⁸ is selected from —OR⁵, (1-4C)alkyl, —C(O)(1-4C)alkyl, —C(O)NR⁴R⁵, (1-4C)alkylamino, di(1-4C)alkylamino, HET-3 wherein the ring is unsubstituted, (1-4C)alkoxy(1-4C)alkyl, hydroxy(1-4C)alkyl and —S(O)$_p$R⁵;

HET-4 is a 5- or 6-membered, C- or N-linked unsubstituted heteroaryl ring containing 1, 2 or 3 ring heteroatoms independently selected from O, N and S;

p is independently 0, 1 or 2;

m is 0 or 1; and n is 0, 1 or 2;

provided that when m is 0, then n is 1 or 2.

2. A process according to claim 1, wherein in the compound of formula (I), R¹ is hydroxymethyl or methoxymethyl; and X is methyl.

3. A process according to claim 1, wherein in the compound of formula (I), m is 1, n is 0 and R² is methylsulfonyl.

4. A process according to claim 1, wherein the compound of formula (I) is a compound of formula (Ia)

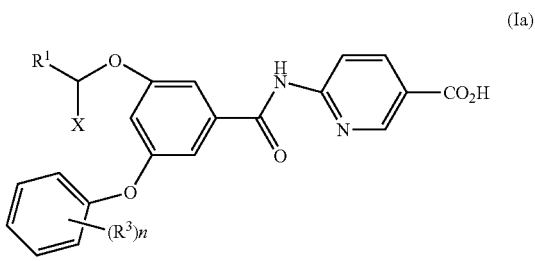

wherein:

R³ is selected from fluoro, chloro, $C_{1-3}$alkyl and $C_{1-3}$alkoxy;

R¹ is selected from methyl and methoxymethyl;

n is 0, 1 or 2; and

X is methyl.

5. A process according to claim 1 wherein step (a)(i) is carried out before step (a)(ii) such that the sequence of reactions comprises:

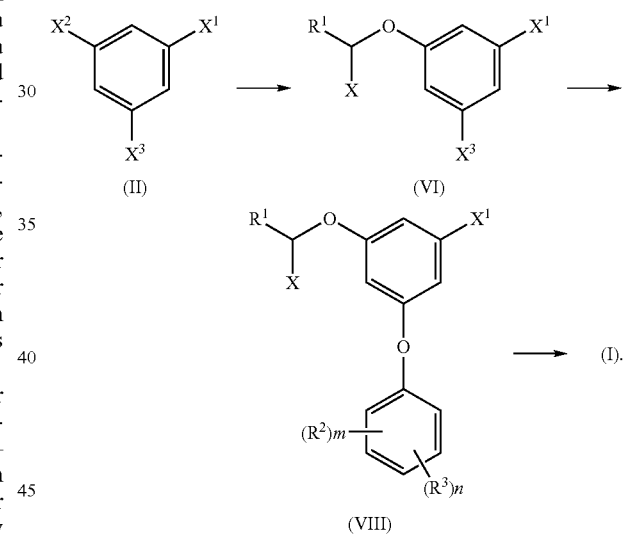

6. A process according to claim 1 wherein step a(ii) is carried out before step a(i) such that the sequence of reactions comprises:

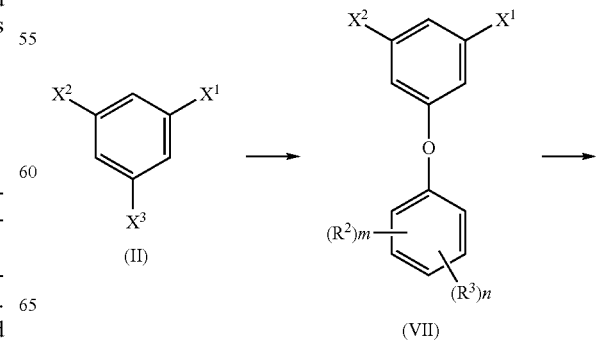

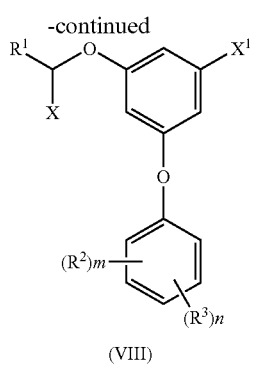

(VIII)

7. A process according to claim 1 for making a compound of formula (Ib), the process comprising:
   (i) reacting difluorobenzonitrile (IIa) with 4-methanesulfonylphenol to give the compound of formula (VIIa);
   (ii) reacting the compound of formula (VIIa) with the compound of formula (IIIa), wherein $R^{1a}$ is methoxymethyl, hydroxymethyl or a protected version of the hydroxymethyl, to give the compound of formula (VIIIa);
   (iii) hydrolyzing the nitrile to give the compound of formula (VIIIb); reacting with a hetreocyclic amine to give the compound of formula (Ib);
   and thereafter optionally:
   i) converting a compound of formula (Ib) into another compound of formula (Ib);
   ii) where $R^{1a}$ is a protected version of hydroxymethyl, removal of the protecting group;
   iii) forming a pro-drug; and/or
   iv) forming a pharmaceutically acceptable salt;

8. A process according to claim 7, wherein $R^{1a}$ is methoxymethyl or tert-butoxymethyl.

9. A process according to claim 7, wherein HET-1 is pyrazolyl, optionally substituted with (1-4C)alkyl.

10. A process according to claim 7, wherein the compound (VIIIb) is isolated as a salt.

11. A process according to claim 7, wherein the compound of formula (Ib), wherein $R^{1a}$ is methoxymethyl or tert-butoxymethyl, is subsequently converted to a compound of formula (Ib) wherein $R^{1a}$ is hydroxymethyl.

12. A process according to claim 11, wherein the compound of formula (VIIIb) is converted to the compound of formula (Ib), wherein $R^{1a}$ is hydroxymethyl, without isolation of the intermediate compound of formula (Ib), wherein $R^{1a}$ is methoxymethyl or tert-butoxymethyl.

13. The compound 3-fluoro-5-[4-(methanesulfonyl)phenoxy]benzonitrile.

14. A compound selected from:
   3-[(1S)-2-methoxy- 1-methylethoxy]-5-[4-methylsulfonyl) phenoxy]benzonitrile and the racemic version;
   3-[(1S)-2-tert-butoxy- 1-methylethoxy]-5-[4-(methylsulfonyl)phenoxy]benzonitrile;
   3-[(1S)-2-tert-butoxy- 1-methylethoxy]-5-[4-(methylsulfonyl)phenoxy]benzoic acid;
   morpholine salt of 3-[(1S)-2-tert-butoxy- 1-methylethoxy]-5-[4-(methylsulfonyl)phenoxy]benzoic acid; and
   tert-butylamine salt of 3-[(1S)-2 -tert-butoxy- 1-methylethoxy]-5 -[4-(methylsulfonyl)phenoxy]benzoic acid.

15. The compound 3-[(1S)-2-tert-butoxy- 1-methylethoxy]-N-(1-methyl-1H-pyrazol-3-yl)-5-[4-(methylsulfonyl)phenoxy]benzamide.